(12) United States Patent
Lee et al.

(10) Patent No.: US 9,668,746 B2
(45) Date of Patent: Jun. 6, 2017

(54) ADJUSTABLE ALLOGRAFT TEMPLATES AND METHODS OF USE

(71) Applicants: Michael S. Lee, Grimes, IA (US); Shannon M. Rush, Pleasanton, CA (US); Jordan P. Grossman, Cuyahoga Falls, OH (US); James Rohl, Prescott, WI (US)

(72) Inventors: Michael S. Lee, Grimes, IA (US); Shannon M. Rush, Pleasanton, CA (US); Jordan P. Grossman, Cuyahoga Falls, OH (US); James Rohl, Prescott, WI (US)

(73) Assignee: Allotemplate, LLC, Grimes, IA (US)

( * ) Notice: Subject to any disclaimer, the term of this patent is extended or adjusted under 35 U.S.C. 154(b) by 479 days.

(21) Appl. No.: 13/937,799

(22) Filed: Jul. 9, 2013

(65) Prior Publication Data
US 2014/0207144 A1 Jul. 24, 2014

Related U.S. Application Data

(63) Continuation-in-part of application No. 13/789,356, filed on Mar. 7, 2013, now abandoned.
(Continued)

(51) Int. Cl.
*A61B 17/15* (2006.01)
*A61B 17/14* (2006.01)
(Continued)

(52) U.S. Cl.
CPC ............ *A61B 17/15* (2013.01); *A61B 17/142* (2016.11); *A61B 17/154* (2013.01);
(Continued)

(58) Field of Classification Search
CPC .............. A61B 17/1645; A61B 17/686; A61B 2017/90
See application file for complete search history.

(56) References Cited

U.S. PATENT DOCUMENTS 5,916,220 A * 6/1999 Masini ................. A61B 17/155
606/87
2004/0260301 A1* 12/2004 Lionberger .......... A61B 17/155
606/88
(Continued)

*Primary Examiner* — Matthew Lawson
*Assistant Examiner* — Amy Sipp
(74) *Attorney, Agent, or Firm* — Davis, Brown, Koehn, Shors & Roberts, P.C.; Sean D. Solberg

(57) ABSTRACT

Adjustable allograft templates and methods of use are disclosed where a template for resecting a tissue region may generally comprise a template frame having a surface for contacting the tissue region and which defines an open area of tissue to be resected. A frame assembly along the template frame may be translatable relative to the template to adjust a size of the open area of tissue to be resected. One or more inner guidance slots may be defined along the frame such that the inner guidance slots are spaced relative to one another to define the tissue within the open area to be resected from a patient. Additionally, one or more outer guidance slots may also be defined along the frame and aligned adjacent to the inner guidance slots. The outer guidance slots may be spaced relative to one another to define the tissue to be resected from a donor.

20 Claims, 25 Drawing Sheets

Related U.S. Application Data

(60) Provisional application No. 61/756,214, filed on Jan. 24, 2013.

(51) Int. Cl.
*A61F 2/42* (2006.01)
*A61F 2/46* (2006.01)
*A61B 90/00* (2016.01)

(52) U.S. Cl.
CPC ... *A61B 2090/034* (2016.02); *A61B 2090/062* (2016.02); *A61B 2090/3937* (2016.02); *A61F 2/4202* (2013.01); *A61F 2002/4649* (2013.01)

(56) References Cited

U.S. PATENT DOCUMENTS

| | | | |
|---|---|---|---|
| 2005/0203531 A1* | 9/2005 | Lakin | A61B 17/155 606/87 |
| 2006/0293681 A1* | 12/2006 | Claypool | A61B 17/155 606/87 |
| 2011/0046629 A1* | 2/2011 | Green, II | A61B 17/155 606/88 |
| 2013/0165936 A1* | 6/2013 | Myers | A61B 17/17 606/80 |
| 2013/0325021 A1* | 12/2013 | Sordelet | A61B 17/155 606/89 |

* cited by examiner

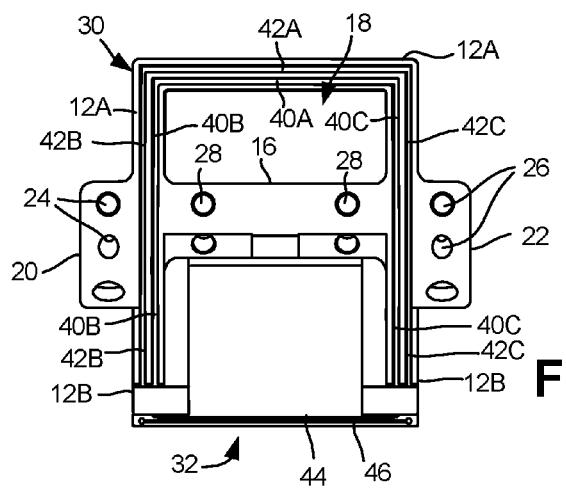
FIG. 2A
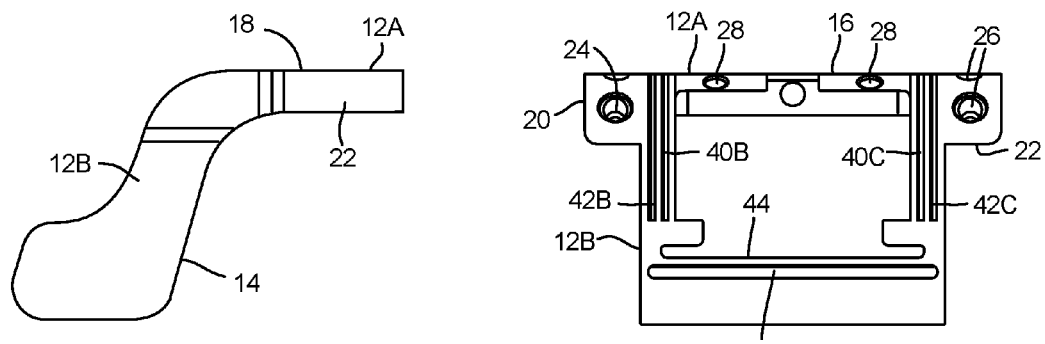
FIG. 2B
FIG. 2C
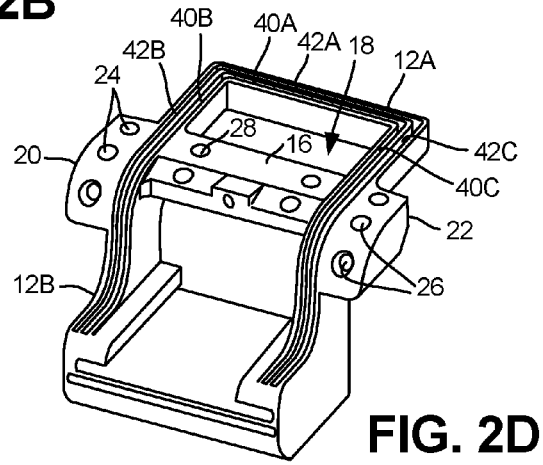
FIG. 2D

ADJUSTABLE ALLOGRAFT TEMPLATES AND METHODS OF USE

CROSS-REFERENCE TO RELATED APPLICATIONS

This application is a continuation-in-part of U.S. application Ser. No. 13/789,356 filed Mar. 7, 2013, which claims the benefit of priority to U.S. Prov. App. 61/756,214 filed Jan. 24, 2013, each of which is incorporated herein by reference in its entirety.

FIELD OF THE INVENTION

The present invention relates to methods and apparatus for resecting allogeneic grafts and implanting them in a controlled manner. More particularly, the present invention relates to methods and apparatus for resecting allogeneic grafts and implanting them in a patient in a controlled manner through use of an allograft template.

BACKGROUND OF THE INVENTION

An osteochondral lesion (osteochondritis dissecans or OCD) is an injury or small fracture of the cartilage surface of the talus which typically occurs via a crush or injury to the surface of the bone during the abnormal motion of the ankle in a sprain. The OCD sits on the medial or lateral shoulder of the talar dome and is situated on the top and the side of the joint surface. The talus bone is part of the collection of bones which forms the lower part of the ankle joint.

With an inversion or eversion stress on the ankle, the talus and tibia and/or fibula will contact each other with massive stress, resulting in a compression or shear stress on the surface of the talus and underlying injury.

In an ankle allograft replacement, an entirely new joint surface (made of bone and cartilage harvested from a fresh cadaver) is typically implanted instead of replacing the ankle joint with a replacement made of metal and plastic. The operation involves removal of a segment of bone and cartilage from the recipient ankle and identical bone cuts made on the ankle cadaver graft.

A cutting jig is typically used to harvest the ankle joint from the cadaver ankle. The block is fixed on to the cadaver (e.g., using one or more K-wires) and the cuts are made to remove the ankle joint which is then implanted into the recipient. Properly fitting a donor bone section into the resection site for a patient is important for recovery time, longevity, and performance for the patient.

However, such cutting jigs are time-consuming to set up and use and may not enable enough of a precise cut for providing a bone graft suitable for resection and implantation. Such an ill-fitting graft may subsequently increase the time for bone in-growth and patient recovery time. Moreover, part of the imprecise cuts may occur because of improper offsetting of the jigs in failing to account for kerf losses incurred when cutting into the bone due to the saw or blade.

Accordingly, there exists a need for methods and apparatus which facilitate procedures such as calcaneal osteotomy procedures by providing for easier and more accurate blade positioning and adjustment features and which provide for shorter procedure times.

SUMMARY OF THE INVENTION

An allograft template may be used as a cutting jig which allows for en bloc resection and grafting of bone between a donor and a patient. The template may be sized in various configurations such that the template may be used for resection and grafting along various regions of the body. Hence, while one particular application for the template may be for resection and grafting to correct for osteochondral lesions along the talus bone, the template may be used in various alternative orthopedic procedures.

The allograft template may facilitate guidance of the saw to allow for resection of a donor graft in a size which is slightly larger than the portion of bone to be resected from the patient bone. Because the same template may be used between the donor and the patient, the cuts may be maintained in a consistent manner between the resection sites. The cuts may be formed in a parallel or angled manner depending upon the angling of the guidance slots defined along the template. Moreover, by accounting for kerf losses in the bone due to the saw cuts, the resection sizes may be offset accordingly by the template. The resulting donor graft may be implanted in the patient resection site resulting in a press-fit which backfills the patient resection site and ensures a secure graft. Hence, the allograft template reduces errors in forming a resection site in the bone of the patient and further reduces errors (e.g., errors resulting from thickness of the blade, measurement errors, cutting errors, etc.) in the forming and extraction of the graft from the bone of the donor.

Generally, a template for resecting a tissue region may comprise a template frame having a surface for contacting the tissue region and which defines an open area of tissue to be resected, one or more inner guidance slots defined along the frame, where the inner guidance slots are spaced relative to one another to define the tissue within the open area to be resected from a patient, and one or more outer guidance slots defined along the frame and aligned adjacent to the inner guidance slots, where the outer guidance slots are spaced relative to one another to define the tissue to be resected from a donor.

One example of a method of resecting the tissue region may generally comprise securing the template frame upon a first tissue region to be resected, where the frame defines an open area of the first tissue to be resected, resecting the first tissue by cutting along one or more inner guidance slots defined along the frame, removing the template frame from the first tissue region, securing the template frame upon a second tissue region to be resected, where the frame defines the open area of the second tissue to be resected, and resecting the second tissue by cutting along one or more outer guidance slots defined along the frame.

In one variation of an allograft template assembly, the template may generally comprises a first portion of a frame which may lie along a first plane and a second curved portion which may extend or curve in an arcuate manner away from the frame along a second plane. The frame and curved portion may together form a framed opening which defines the border or framed boundary of the bone portion to be either grafted and/or resected. Moreover, the frame and curved portion may define one or more frame guidance slots and guidance slots along the template assembly for defining the tissue area to be cut and for guiding the saw and/or blade along the tissue, as described in further detail below.

Additionally, the frame and/or curved portion may incorporate a cross member extending between the frame members for providing structural support and stability and also for optionally providing one or more cross member openings through which pins or wires may be passed for securement to the underlying tissue or bone, such as the bone to be resected from a patient. To facilitate handling of the template assembly during a grafting and/or resection procedure, one or more handles may be attached, for instance, along the cross member to extend from the template assembly. Handles may be positioned along other sections of the template assembly if so desired.

One or more supporting flanges may also be optionally integrated to extend outwardly along one or both sides of the frame and/or curved portion. These supporting flanges may define one or more flange openings defined at various angles therethrough. Pins or wires may be passed through these flange openings for securement to the underlying tissue or bone, such as the bone of the donor at regions adjacent to the resected bone.

The frame and curved portion may define an inner guidance slot defined along the length and an additional outer guidance slot may also be defined along the length of the frame and part of curved portion in parallel with the inner guidance slot. With the inner and outer guidance slots defined parallel to one, the saw or blades may be inserted through or along a respective guidance slot such that the saw or blade become transversely oriented relative to the inner guidance slot and outer guidance slot.

In use, the template assembly may be used to resect a portion of bone from the bone of the donor which is slightly larger than the corresponding resected opening in the bone of the patient. Hence, the resulting resected bone segment from the donor may result in a graft which can be press-fit into the patient's bone. By accounting for the kerf loss in the bone or tissue typically due to the width of the saw or blade passing through bone or tissue, the width of the resected bone portion may be sized in a consistent and repeatable manner. The opposed inner guidance slots may be separated from one another to have a width of the patient's bone plus the kerf loss to be equal to the width of the donor's bone minus the kerf loss. Hence, the inner guidance slots may define the width of the resected bone to be cut from the patient. Similarly, length of the bone resected from the patient may be equal to the length of the donor graft bone minus the kerf loss. Similarly, the length of the framed opening may marked by the inner guidance slot which may define the length of the resected bone to be cut from the patient.

Because the bone graft to be resected from the donor bone is generally larger than the resected opening in the patient bone, the corresponding bone graft dimensions to be cut from the donor may be demarcated by the outer guidance slots. Thus, the width of the bone graft to be resected from the donor bone may be defined by the outer guidance slots. Generally, the outer guidance slots may have dimensions which account for the saw kerf when cutting the graft from the donor site. Thus, the outer guidance slots may be sized by estimating the graft dimensions as the resection length plus kerf loss, resection width plus kerf loss, and resection thickness plus kerf loss.

As above, the thickness of the bone to be resected from the patient is equal to the thickness of the donor bone minus the kerf loss due to the saw or blade. The corresponding height of the bone to be resected from the patient may be seen by the height extending from the contact surface of frame to the inner guidance slot and the height of the bone to be grafted from the donor may be seen by the height extending from the contact surface of frame to the outer guidance slot.

Once the template assembly has been situated and secured against the region of the bone to be resected, a saw may be initially inserted along the inner guidance slot and advanced into and through the bone to a predetermined depth, such as the length of the template assembly, until the bone has been cut completely over the width of inner guidance slot. The saw may then be removed or left in place within the bone. The saw (or an additional saw) may then be introduced along the inner guidance slot to complete the cut within the bone to a predetermined depth, such as the depth defined by the template assembly. Similarly, additional cuts may be made along the inner guidance slots by the same or additional saws to result in a completely resected bone segment.

The same or additional saws may then be inserted and guided within the respective outer guidance slots to cut along the predetermined paths for resecting a bone section from the donor bone which is slightly larger than the portion resected from the patient bone but which still has the same relative dimensions and consistent cuts to result in a press-fit graft which is consistently sized between donor and patient.

As the saw or blade is inserted along the guidance slots, the depth to which the cuts are made may be controlled through a number of different mechanisms. In one example, the saw may have one or more markers or visual indicators (e.g., laser markers) placed upon the surface of the saw to correspond to the desired cutting depth. Such markers or indicators may be consistent between each guidance slot or they may be varied depending upon which guidance slot the saw is inserted within. Alternatively, rather than a marker or visual indicator, the saw may have a projection or protrusion which functions as a stop such that when the projection or protrusion abuts against the guidance slot of the template assembly, then the desired cutting depth has been reached. By maintaining predetermined cutting depths along the guidance slots, consistent resections or grafted bone segments may be maintained between the donor bone and patient bone with minimal damage to surrounding bone or tissue.

In addition to the saws or blades having indicators for monitoring cutting depth, the one or more securement wires, e.g., K-wires, olive wires, pins, etc., which may be used to secure the template assembly to the donor and/or patient bone may also define one or more respective markings or visual indicators along their lengths such as graduations. The markings may be measured against the respective insertion hole to determine the insertion depth into the donor and/or patient bone and/or tissue. By monitoring the securement wire insertion depth, damage to the underlying bone and/or tissue may be minimized but may still ensure that an adequate insertion depth has been achieved to maintain a secure placement of the template assembly relative to the underlying bone.

In one example of use, the portion of bone to be resected from the patient may be cut and removed first and the same template may then be used to resect the bone graft from the donor bone. Alternatively, the donor graft may be resected first and the portion of bone to be resected from the patient may be then resected. In yet another alternative, both the bone of the patient and the bone of the donor may be resected simultaneously by utilizing multiple template assemblies having identical dimensions.

The portion of the bone to be repaired in the patient may be first identified and the template assembly may then be placed into contact against the patient bone such that the framed opening of template assembly surrounds the portion of the patient resected bone to be repaired. With the template assembly initially held in place against the surface of the patient bone, one or more securement wires may be inserted through the template assembly, e.g., through the openings defined along the cross-member, while monitoring their insertion depth to hold the template in place relative to the bone surface. Because the damaged patient resected bone bounded by the framed opening is to be removed from the patient bone, the one or more securement wires may be inserted specifically into the patient resected bone through the cross-member such that the surrounding bone may remain undamaged or untouched by the securement wires.

With the template assembly secured in place, the saw may be inserted through inner guidance slot and the bottom cut may be made into the bone first while monitoring and/or measuring the cutting depth via the optional graduations along the saw. The saw may be optionally left in place within the bone and the remaining cuts may then be made. Alternatively, the same saw and/or additional saws may be then inserted along the side inner guidance slots to make the cuts into the patient bone while monitoring and/or measuring the cutting depth. The same saw or additional saws may then be used to make the final cut along the distal inner guidance slot. The patient resected bone may be removed by tensioning the handle and/or securement wires to leave the resected channel for grafting. In other variations, the order of the cuts into the bone may be altered as suitable or desired. For instance, the initial cut into the bottom of the patient resected bone may be followed by cuts into the distal end of the bone followed by subsequent cuts along the sides of the bone. In yet other alternatives, an initial cut may be made along the distal end of the patient resected bone followed by cuts along the bottom and/or sides of the bone.

The patient resected bone may be removed from the template assembly which may then be placed into contact against the donor bone such that the framed opening of the template bounds a region of the donor resected bone similar to the patient resected bone. With the handle used to hold the template in place, one or more securement wires may then be passed through the openings defined along the supporting flanges which extend exteriorly of the framed opening and into the underlying donor bone while optionally measuring the insertion depth of the securement wires. Because the donor resected bone is to be removed from the donor bone and grafted into the resected channel defined by the patient resected bone, the one or more securement wires may be inserted through the supporting flanges to secure the template assembly relative to the donor bone. This ensures that the graft donor resected bone remains undamaged by any additional openings which may otherwise be created by the insertion of securement wires.

In yet another variation of the template assembly, a template may utilize a first template for placement upon a bone of the donor and an additional second template for placement upon a bone of the patient. A common guide housing may be utilized between the two different templates to maintain consistency between the resected bone from the patient and the resected bone from the donor for grafting into the patient bone.

Generally, such a template assembly may comprise a first template for placement upon a bone of a donor, where the first template comprises a first frame which defines an open area of tissue upon the bone of the donor, a second template for placement upon a bone of a patient, where the second template comprises a second frame which defines an open area of tissue upon the bone of the patient, and a guide housing which defines a receiving channel for tissue, where the guide housing is further configured to engage the open area of the first template and the open area of the second template.

One example for using the template assembly may generally comprise securing the first template upon a first tissue region to be resected, where the first template defines an open area of the first tissue to be resected, engaging the guide housing along the first template over the open area of the first tissue, resecting the first tissue by cutting along first guidance slots defined between the first template and the guide housing, engaging the second template upon a second tissue region to be resected, where the second template defines an open area of the second tissue to be resected, engaging the guide housing along the second template over the open area of the second tissue, and resecting the second tissue by cutting along second guidance slots defined between the second template and the guide housing.

An internal saw guide assembly may utilize a guide housing between the bone of the patient and the bone of the donor to maintain cutting consistency. The guide housing may form a housing which is open along the portion which contacts the surface of the bone (both donor and patient) to be resected. The guide housing may have a handle which extends from the housing and may further define channels along the sides and bottom portion of the housing for guiding and/or receiving one or more saws. The top of the guide housing may define one or more openings through which one or more corresponding securement wires or pins may be inserted for securing the guide housing to the underlying bone.

The guide housing may be engaged with or inserted along a donor template as well as a corresponding patient template, as described below. The donor template may define one or more openings through which securement wires or pins may be inserted for securing the template to the donor bone. The donor template may accordingly define a contact surface for placement along or upon the underlying bone as a well as a curved template portion to facilitate conformance against the bone surface.

In use, a patient template which defines a curved template portion and a contact surface for conformance against the underlying patient bone may be placed upon a region of the patient bone such that the framed opening bounds the portion of the patient resected bone which is damaged and which is to be replaced by a graft. The patient template may be maintained in place against the patient bone by the handle attached to the template and/or by one or more securement wires which may be inserted through the template and into the underlying bone. A first saw may be inserted through a saw guide defined along the template to a predetermined depth. Then the guide housing may be advanced along and within the framed opening such that the guide housing is fully engaged within the template. The guide housing may be secured and maintained against the patient template as well as the patient bone by inserting one or more securement wires or pins through the openings defined through the guide housing. Moreover, the securement wires or pins may be secured directly to the patient respected bone to be removed and replaced by the graft.

With the guide housing secured within the patient template and against the patient resected bone, a second saw may be inserted between the patient template and the distal portion of the guide housing. The saw may be inserted to a predetermined depth, e.g., by one or more graduations defined along the saw body, or until the distal cutting edge comes into contact against the first saw which may be left in place within the bone to define a stop or boundary to prevent the further advancement of the saw into the underlying patient bone. The remaining saws may be advanced along the sides of the guide housing and within the patient template to completely resect the patient resected bone within the guide housing.

With the patient bone resected, the donor bone may also be resected in a similar manner but with a second donor template which defines an opening which corresponds in size with the patient template framed opening. The donor template may similarly define a contact surface for placement against the donor bone such that the opening of the donor template frames the donor resected bone to be grafted. Hence, the framed donor resected bone may be consistent in size with the channel defined by the patient resected bone in the patient bone. The donor template similarly defines one or more openings through which the securement wires or pins may be inserted away from the donor resected bone to maintain the integrity of the graft. The donor template may define a receiving channel along the template for receiving the guide housing in a consistent orientation. Hence, the same guide housing used to create the patient resected bone may be advanced into a sliding engagement optionally through the receiving channel upon the donor bone.

As with resection of the patient bone, once the guide housing is secured along the donor template, the first saw may be advanced along the bottom portion of the donor resected bone. The additional saws may be advanced into contact against the first saw to form the distal end of the donor resected bone and the remaining saws may be advanced along the respective sides of the guide housing between the donor template to completely resect the donor resected bone within the guide housing. The donor resected bone may then be removed from the donor bone and grafted into the channel formed by the patient resected bone.

In yet another variation of a resection template, a guide template may be configured to be placed against an anterior portion of a bone to be resected. The anterior guide template may be configured to form a bone receiving channel defined by contact surfaces formed along template walls extending partially from a transversely oriented guide surface. A handle may extend from the anterior guide template to facilitate handling of the template and the guide surface may define one or more openings for the passage of securement wires or pins into the underlying bone to be resected. The guide surface may also define one or more guidance slots which may be aligned in a transverse orientation such that one or more corresponding saws may be inserted into the respective slots to cut the bone contained within the bone receiving channel. Other variations of an anterior resection template may omit the bone receiving channel.

BRIEF DESCRIPTION OF THE DRAWINGS

FIGS. 2A to 2D show respective top, side, end, and perspective views of the template of FIG. 1A.

DETAILED DESCRIPTION OF THE INVENTION

An allograft template may be used as a cutting jig which allows for en bloc resection and grafting of tissue, namely portions of bone, between a donor and a patient. The template may be sized in various configurations such that the template may be used for resection and grafting along various regions of the body. Hence, while one particular application for the template may be for resection and grafting to correct for osteochondral lesions along the talus bone, the template may be used in various alternative orthopedic procedures.

The allograft template may facilitate guidance of the saw to allow for resection of a donor graft in a size which is slightly larger than the portion of bone to be resected from the patient bone. Because the same template may be used between the donor and the patient, the cuts may be maintained in a consistent manner between the resection sites. Moreover, by accounting for kerf losses in the bone due to the saw cuts, the resection sizes may be offset accordingly by the template. The resulting donor graft may be implanted in the patient resection site resulting in a press-fit which backfills the patient resection site and ensures a secure graft. Hence, the allograft template reduces errors in forming a resection site in the bone of the patient and further reduces errors (e.g., errors resulting from thickness of the blade, measurement errors, cutting errors, etc.) in the forming and extraction of the graft from the bone of the donor.

Figure 1A:
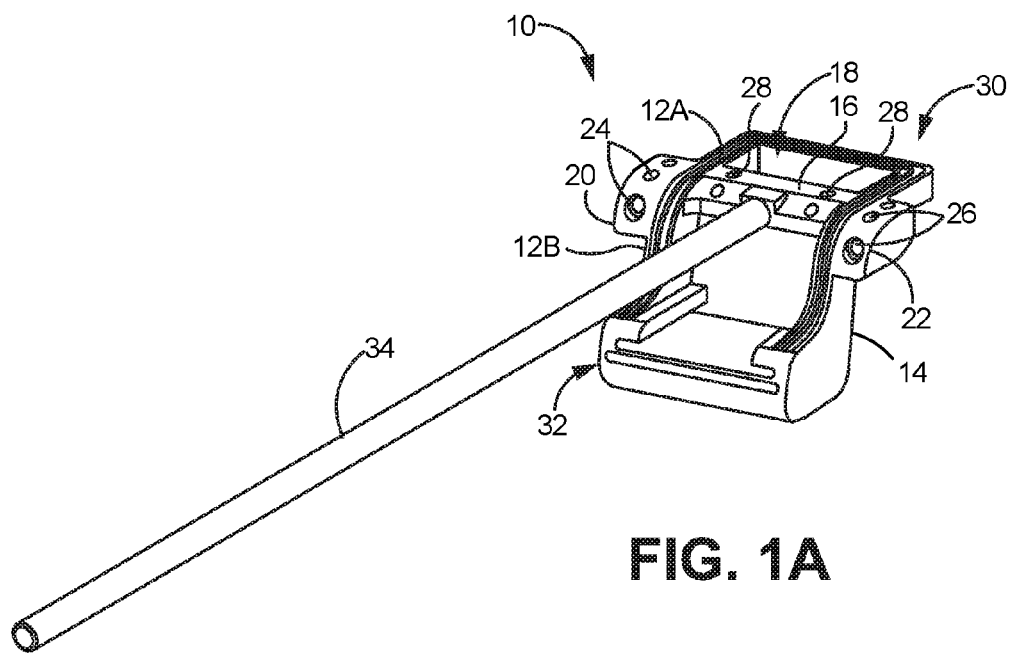
FIGS. 1A and 1B show alternate perspective views of one variation of an allograft template.
Figure 1B:
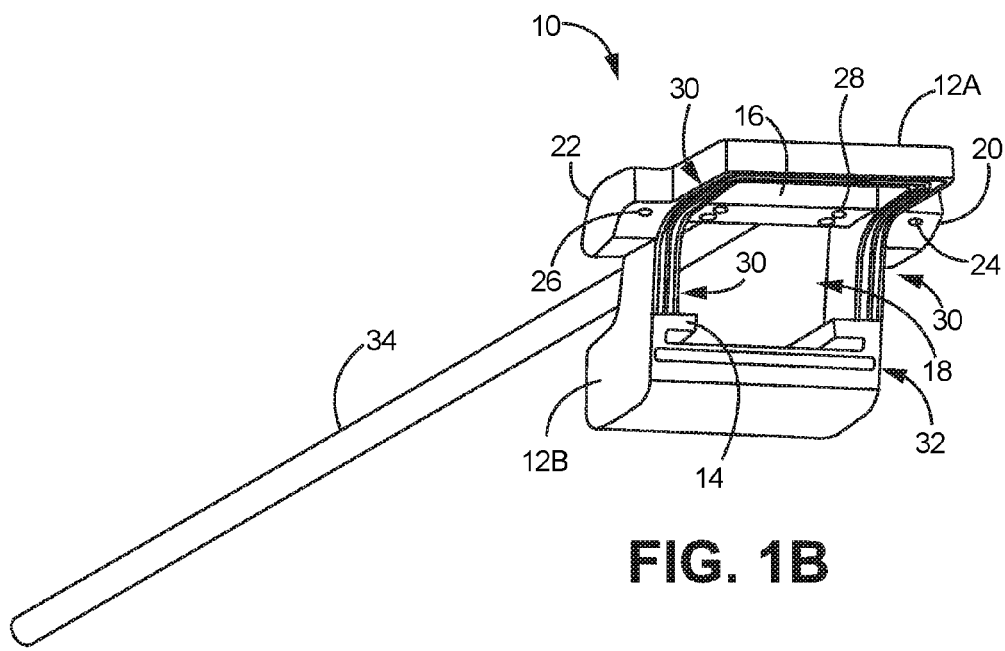

FIGS. 1A and 1B show alternate perspective views of one variation of an allograft template assembly 10 which generally comprises a first portion of a frame 12A which may lie along a first plane and a second curved portion 12B which may extend or curve in an arcuate manner away from the frame 12A along a second plane. The frame 12A and curved portion 12B may together form a framed opening 18 which defines the border or framed boundary of the bone portion to be either grafted and/or resected. Moreover, the frame 12A and curved portion 12B may define one or more frame guidance slots 30 and guidance slots 32 along the template assembly 10 for defining the tissue area to be cut and for guiding the saw and/or blade along the tissue, as described in further detail below.

The template assembly 10 may also define a contact surface 14 for placement against the surface of the bone or tissue to be grafted and/or resected. The contact surface 14 may simply follow the frame 12A and curved portion 12B or the contact surface 14 may be specially contoured to conform to any number of tissue regions such as the superior region of a talus bone. Additionally, the frame 12A and/or curved portion 12B may incorporate a cross member 16 extending between the frame 12A members for providing structural support and stability and also for optionally providing one or more cross member openings 28 through which pins or wires may be passed for securement to the underlying tissue or bone, such as the bone to be resected from a patient. To facilitate handling of the template assembly 10 during a grafting and/or resection procedure, one or more handles 34 may be attached, for instance, along the cross member 16 to extend from the template assembly 10. Handles may be positioned along other sections of the template assembly 10 if so desired.

One or more supporting flanges 20, 22 may also be optionally integrated to extend outwardly along one or both sides of the frame 12A and/or curved portion 12B. These supporting flanges 20, 22 may define one or more flange openings 24, 26 defined at various angles therethrough. Pins or wires may be passed through these flange openings 24, 26 for securement to the underlying tissue or bone, such as the bone of the donor at regions adjacent to the resected bone.

FIGS. 2A to 2D show respective top, side, end, and perspective views of the template assembly 10 with the handle removed for clarity. Moreover, the frame 12A and curved portion 12B may be seen with an inner guidance slot 40A, 40B, 40C defined along the length of frame 12A and part of curved portion 12B. An additional outer guidance slot 42A, 42B, 42C may also be seen along the length of frame 12A and part of curved portion 12B in parallel with the inner guidance slot 40A, 40B, 40C. With the inner and outer guidance slots defined parallel to one another along frame 12A and curved portion 12B, the saw or blades may be inserted through or along a respective guidance slot such that the saw or blade become transversely oriented relative to the inner guidance slot 44 and outer guidance slot 46 of guidance slot 32. The saw or blade inserted along the inner and outer guidance slots 44, 46 may be oriented to be parallel with the handle and/or transverse to the cuts made by the saw or blade being inserted through the inner guidance slots 40A, 40B, 40C or the outer guidance slots 42A, 42B, 42C.

While the size of template assembly 10 may be varied according to the size of the bone or tissue to be resected as well as the shape of the anatomy within the body, the template assembly 10 may be varied in dimension. For illustrative purposes, the variation shown may generally have a width of about 0.90 inches and a height of about 0.75 inches. The supporting flanges 20, 22 may also have a width of about 0.19 inches while the inner guidance slots 40A, 40B, 40C and the outer guidance slots 42A, 42B, 42C may be sized to have a width to accommodate any number of saws or blades, e.g., 0.02 inches. Typical surgical saw blades (e.g., available from Synvasive®, Stryker®, etc.) may range in thickness from, e.g., 0.005, 0.010, 0.015 inches or more; hence, a guidance slot width of 0.02 inches is sufficient to accommodate many surgical saws although the slot width may be sized to be greater if needed or desired, as well as the angle of control the template places on the blade may be varied. For example a 2.5 degree angle on the outer slot can help create a tighter press fit, as described in further detail herein. The remaining inner and outer guidance slots 44, 46 may also have width, e.g., ranging from 0.02 to 0.04 inches.

Figure 3A:
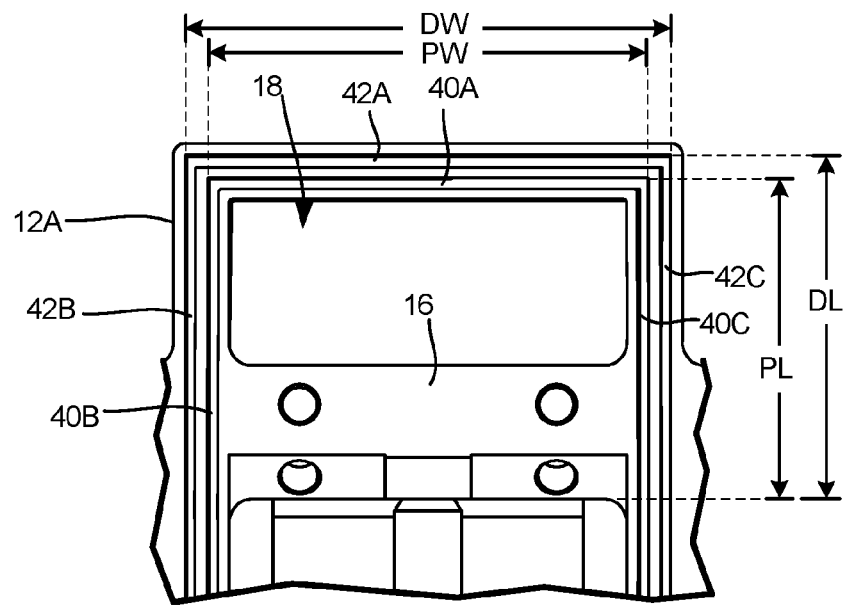
FIGS. 3A and 3B show top and end views of the template to illustrate the inner and outer guidance slots which are adjacent and parallel to one another.

In use, the template assembly 10 may be used to resect a portion of bone from the bone of the donor which is slightly larger than the corresponding resected opening in the bone of the patient. Hence, the resulting resected bone segment from the donor may result in a graft which can be press-fit into the patient's bone. By accounting for the kerf loss in the bone or tissue typically due to the width of the saw or blade passing through bone or tissue, the width of the resected bone portion may be sized in a consistent and repeatable manner. As shown in the top view of template assembly 10 in FIG. 3A, the opposed inner guidance slots may be separated from one another to have a width of the patient's bone plus the kerf loss to be equal to the width of the donor's bone minus the kerf loss. Hence, the inner guidance slots 40B, 40C may define the width of the resected bone PW to be cut from the patient. Similarly, length of the bone resected from the patient may be equal to the length of the donor graft bone minus the kerf loss. As shown in FIG. 3A, the length of the framed opening 18 may marked by the inner guidance slot 40A which may define the length of the resected bone PL to be cut from the patient.

Because the bone graft to be resected from the donor bone is generally larger than the resected opening in the patient bone, the corresponding bone graft dimensions to be cut from the donor may be demarcated by the outer guidance slots 42A, 42B, 42C. Thus, the width of the bone graft DW to be resected from the donor bone may be defined by the guidance slots 42B, 42C. Similarly, the length of the bone graft DL to be resected from the donor bone may be defined by the guidance slot 42A. Generally, the outer guidance slots 42A, 42B, 42C may have dimensions which account for the saw kerf when cutting the graft from the donor site. Thus, the outer guidance slots may be sized by estimating the graft dimensions as the resection length plus kerf loss, resection width plus kerf loss, and resection thickness plus kerf loss.

Figure 3B:
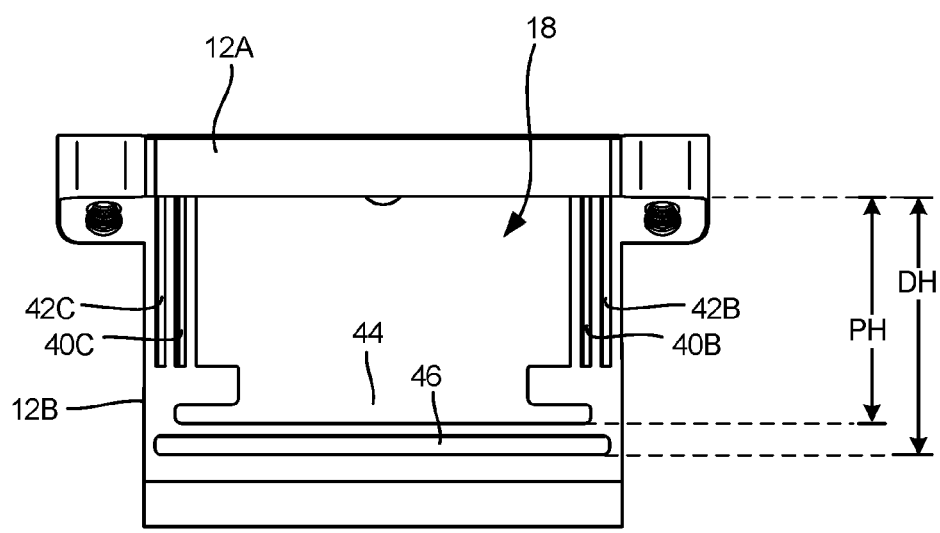

Likewise, the height of the bone to be resected may be demarcated by the guidance slots as shown in the end view of FIG. 3B. As above, the thickness of the bone to be resected from the patient is equal to the thickness of the donor bone minus the kerf loss due to the saw or blade. The corresponding height of the bone to be resected from the patient may be seen by the height PH extending from the contact surface of frame 12A to the inner guidance slot 44 and the height of the bone to be grafted from the donor may be seen by the height DH extending from the contact surface of frame 12A to the outer guidance slot 46.

Figure 4A:
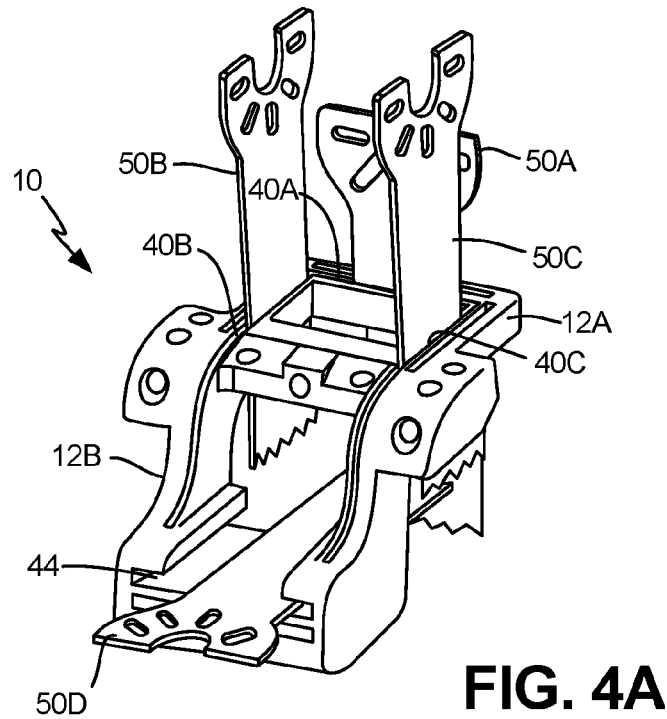
FIG. 4A shows a perspective view of a template with saws inserted through each of the inner guidance slots.
Figure 4B:
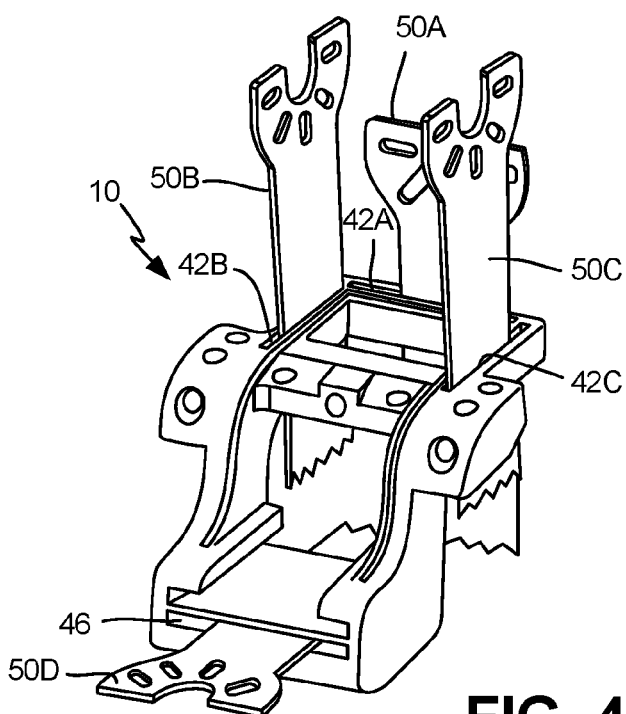
FIG. 4B shows a perspective view of a template with saws inserted through each of the outer guidance slots.

FIGS. 4A and 4B illustrate perspective views of the frame assembly 10 with multiple saws or blades inserted within their respective guidance channels to show the saw and template assembly interaction. The example shown in FIG. 4A illustrates how the template assembly 10 may be used to resect a portion of bone to be replaced from a patient. Although multiple saws are shown for illustrative purposes, a single saw or blade may be used to sequentially form the cuts defined by each slot. Alternatively, multiple blades may be used simultaneously along one or more guidance slots to facilitate the bone resection.

In either case, once the template assembly 10 has been situated and secured against the region of the bone to be resected (in this example the bone of the patient), a saw 50D may be initially inserted along the inner guidance slot 44 and advanced into and through the bone to a predetermined depth, such as the length of the template assembly 10, until the bone has been cut completely over the width of inner guidance slot 44. The saw 50D may then be removed or left in place within the bone. The saw 50D (or an additional saw 50A) may then be introduced along the inner guidance slot 40A to complete the cut within the bone to a predetermined depth, such as the depth defined by the template assembly 10. Similarly, additional cuts may be made along the inner guidance slots 40B, 40C by the same or additional saws 50B, 50C to result in a completely resected bone segment.

The same template 10 is also shown in the perspective view of FIG. 4B where the template assembly 10 may then be placed or otherwise secured to the bone of a donor. The same or additional saws 50A, 50B, 50C, 50D may then be inserted and guided within the respective outer guidance slots 42A, 42B, 42C, 46 to cut along the predetermined paths for resecting a bone section from the donor bone which is slightly larger than the portion resected from the patient bone but which still has the same relative dimensions and consistent cuts to result in a press-fit graft which is consistently sized between donor and patient.

As the saw or blade is inserted along the guidance slots, the depth to which the cuts are made may be controlled through a number of different mechanisms. In one example, the saw may have one or more markers or visual indicators (e.g., laser markers) placed upon the surface of the saw to correspond to the desired cutting depth. Such markers or indicators may be consistent between each guidance slot or they may be varied depending upon which guidance slot the saw is inserted within. Alternatively, rather than a marker or visual indicator, the saw may have a projection or protrusion which functions as a stop such that when the projection or protrusion abuts against the guidance slot of the template assembly 10, then the desired cutting depth has been reached. By maintaining predetermined cutting depths along the guidance slots, consistent resections or grafted bone segments may be maintained between the donor bone and patient bone with minimal damage to surrounding bone or tissue.

Figure 5:
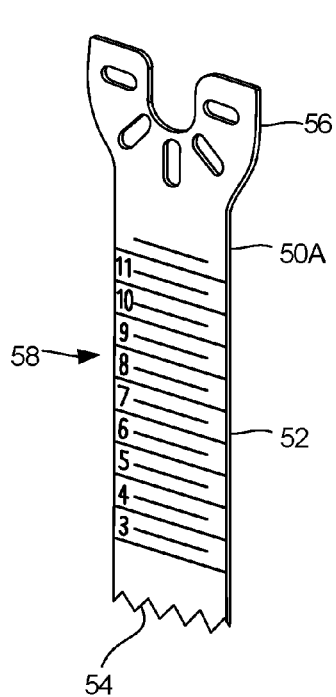
FIG. 5 shows a perspective view of one variation of a graduated saw having indicators for determining a cutting depth.
Figures 6A, 6B:
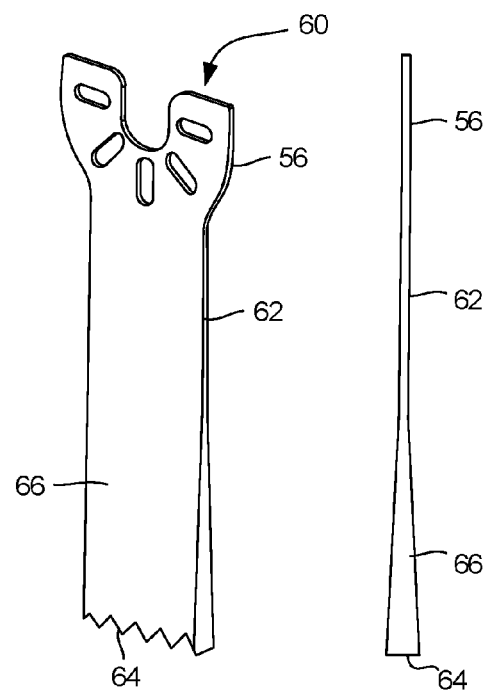
FIGS. 6A and 6B show perspective and side views of another variation of a saw having a tapered cutting portion.

FIG. 5 illustrates an example of a surgical saw 50A having a saw body 52 terminating in a distal cutting edge 54 and having a handle portion 56 of the proximal edge. The body 52 may define one or more graduations 58 along the length of the body 52 such that the cutting depth may be measured during a resection procedure by comparing the indicated depth against the guidance slot of the template assembly 10. FIGS. 6A and 6B show perspective and side views of an alternative saw 60 having a saw body 62 and a tapered portion 66 which tapers into a gradually thicker section relative to the saw body 62 and terminates in a cutting edge 64. Saw body 62 may also define one or more graduations along the body 62 for gauging the cutting depth.

Figure 7:
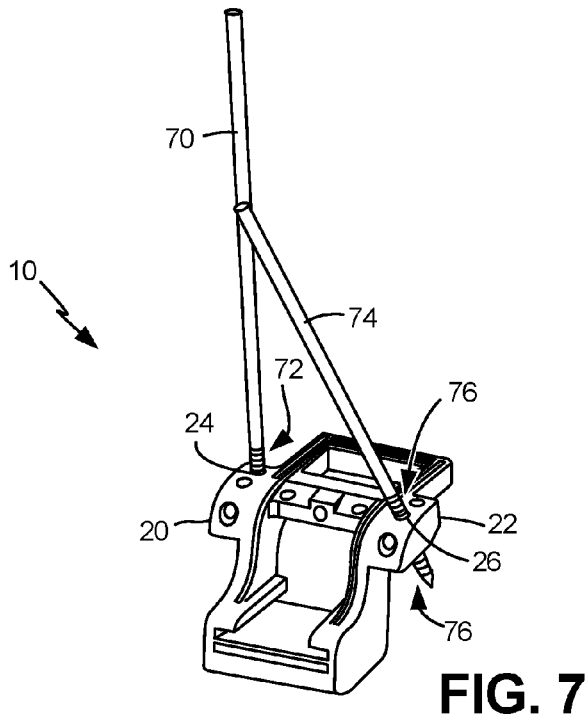
FIG. 7 shows a perspective view of a template having graduated securement pins or wires for determining an insertion depth into the bone or tissue.

In addition to the saws or blades having indicators for monitoring cutting depth, the one or more securement wires 70, 74, e.g., K-wires, olive wires, pins, etc., which may be used to secure the template assembly 10 to the donor and/or patient bone may also define one or more respective markings or visual indicators along their lengths such as graduations 72, 76 as shown in the perspective view of FIG. 7. The markings may be measured against the respective insertion hole to determine the insertion depth into the donor and/or patient bone and/or tissue. By monitoring the securement wire 70, 74 insertion depth, damage to the underlying bone and/or tissue may be minimized but may still ensure that an adequate insertion depth has been achieved to maintain a secure placement of the template assembly 10 relative to the underlying bone.

Figure 8A:
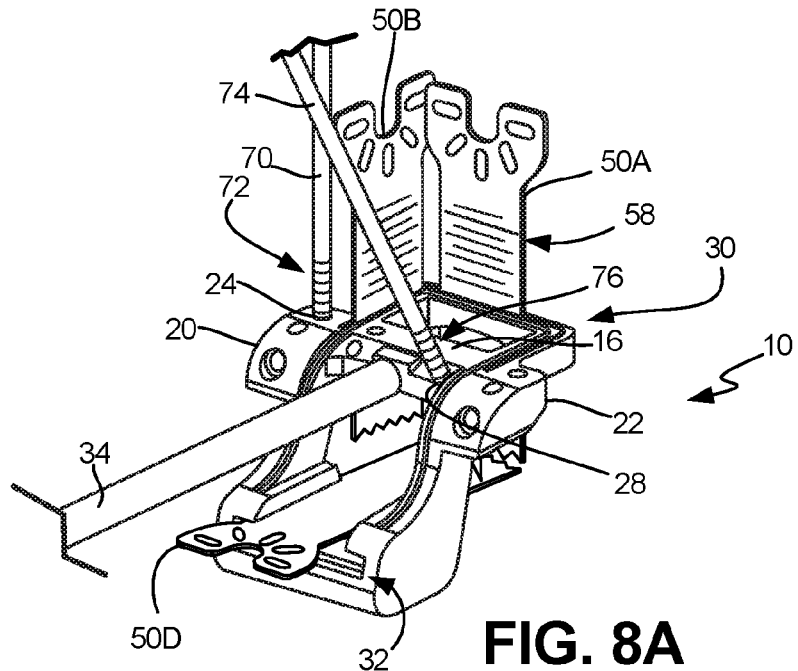
FIGS. 8A and 8B show perspective views of a template having both saws and securement pins or wires graduated and placed upon a bone for resection.
Figure 8B:
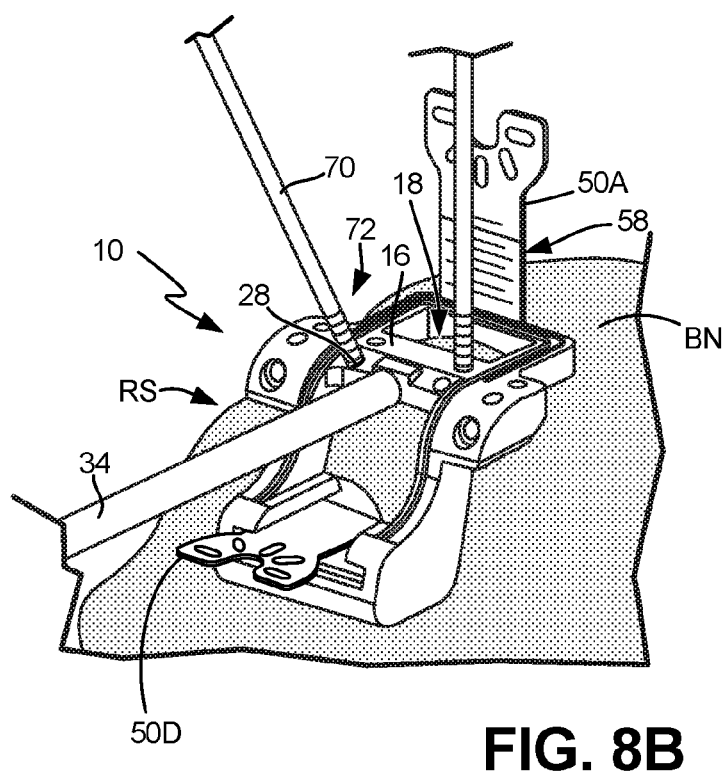

FIG. 8A shows a perspective view of a template assembly having one or more saws 50A, 50B, 50D inserted through a respective guidance slot and securement wires 70, 74 inserted through respective securement openings 24, 28. FIG. 8B shows a perspective view of the template assembly 10 placed against the bone BN. The template assembly 10 may be seen secured to the bone by the insertion of the securement wire 70 placed through opening 28 defined along cross-member 16 to prevent or inhibit movement of the template 10 relative to the bone BN during the resection procedure. The insertion depth of the securement wire 70 may be gauged by the graduations 72 marked against the cross-member 16 to ensure that the securement wire 70 is sufficiently inserted into the underlying bone to be resected RS but not deeply enough to damage bone or tissue beyond the resected portion RS.

With the template assembly 10 secured accordingly, the saw 50D may be inserted through the appropriate guidance slot and the same or additional saws 50A may be inserted through its respective guidance slot to further cut around the bone. As shown, with the graduations 58 marked along the body of saw 50A, the cutting depth may be monitored and measured by the degree to which the saw 50A is cut into the bone relative to the guidance slot.

In one example of use, the portion of bone to be resected from the patient may be cut and removed first and the same template may then be used to resect the bone graft from the donor bone. Alternatively, the donor graft may be resected first and the portion of bone to be resected from the patient may be then resected. In yet another alternative, both the bone of the patient and the bone of the donor may be resected simultaneously by utilizing multiple template assemblies having identical dimensions.

Figure 9A:
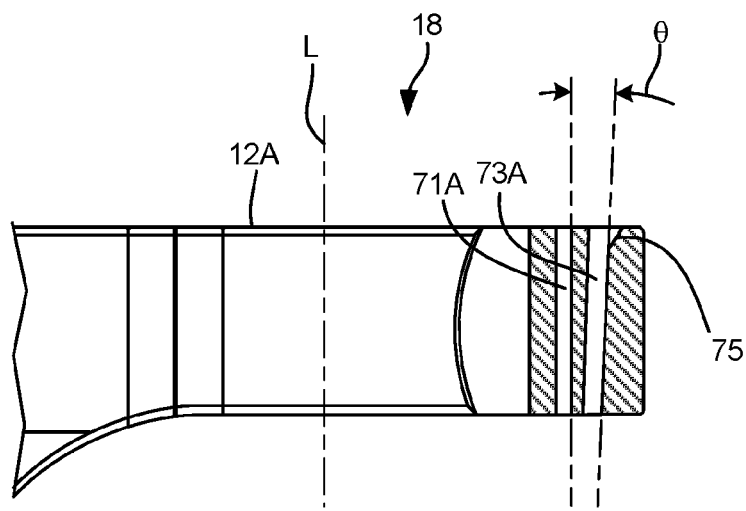
FIGS. 9A to 9D show views of an alternative template assembly having guidance slots, e.g., outer guidance slots, angled for forming tapered surfaces in the underlying resected bone.

In yet another variation of the template assembly, the outer guide 73A along the frame 12A and/or curved portion 12B may be angled relative to a normal axis L defined by the framed opening 18, as shown in the cross-sectional side view of FIG. 9A. While the inner guide 71A may remain relatively parallel with the normal axis L, the outer guide 73A may be angled slightly, e.g., forming an angle of 2.5 degrees relative to the normal axis L and/or inner guide 71A, such that the angle tapers away from the framed opening 18. The degree to which the guidance slots are angled may of course be varied depending upon the degree of taper to be formed along the resected bone and/or channel.

An additional chamfer 75 may be formed along the entry of the outer guide 73A to facilitate the insertion of the saw into the guide. By angling the outer guide 73A in such a manner relative to the inner guide 71A, the saw may be correspondingly guided at an angle along the guide 73A such that the bone graft resected from the donor bone DBN may be formed with tapered sides which may help to form a tighter press-fit graft when implanted into the patient.

In other variations, the inner guide may be angled relative to the normal axis L or both the inner 71A and outer 73A guides may be angled relative to one another and/or relative to the normal axis L of the framed opening 18. In either case, the use of angled guidance slots may be utilized in combination with any of the embodiments described herein as practicable.

Figure 9B:
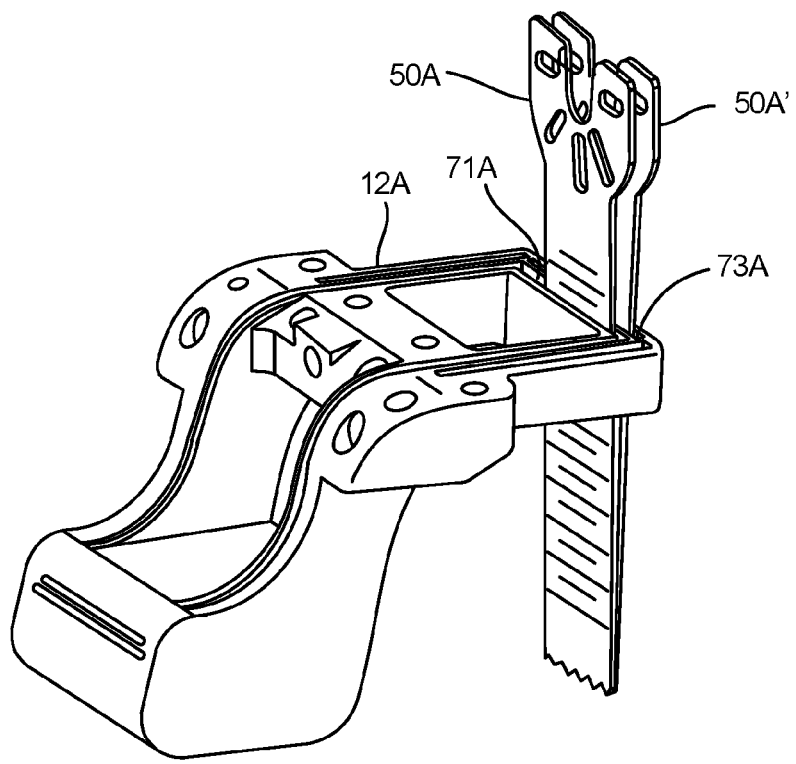
Figure 9C:
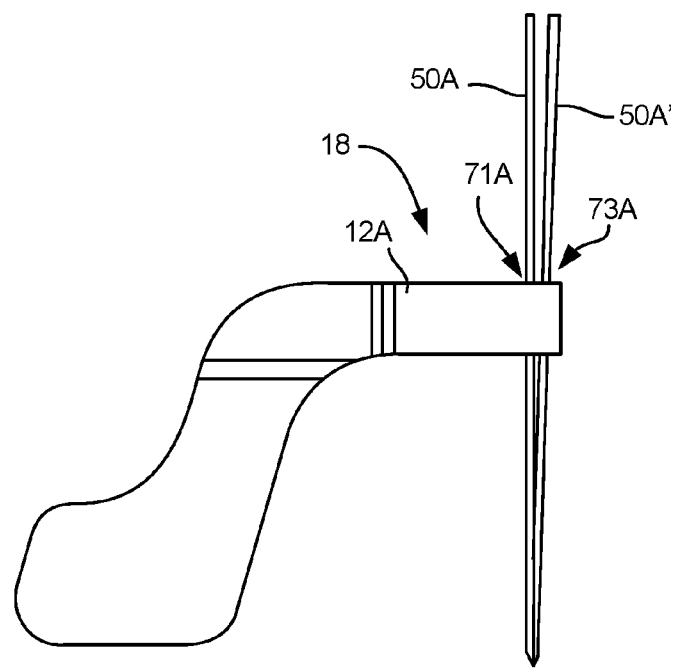

FIG. 9B shows a perspective view of the template assembly with saws 50A and 50A' inserted through respective inner 71A and outer 73A guidance slots to illustrate how the saw 50A' inserted through outer guidance slot 73A may form a tapered cut relative to the cut formed by saw 50A inserted through inner guidance slot 71A when inserted into the underlying bone. FIG. 9C shows a side view also illustrating the angled taper formed by the resulting cuts into the underlying bone.

Figure 9D:
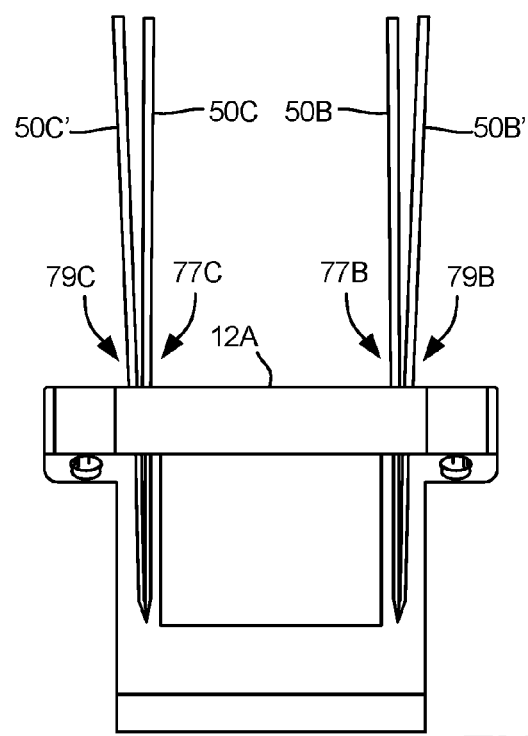

FIG. 9D shows an end view illustrating how the outer slots 79B, 79C defined along the sides of the framed opening 18 may also be formed at an angle relative to the normal axis L and respective inner slots 77B, 77C. The saws 50B and 50C inserted through respective inner guidance slots 77B and 77C may be seen formed relatively parallel to form straight, parallel cuts into the underlying patient bone. In contrast, the saws 50B' and 50C' are illustrated inserted through respective outer guidance slots 79B and 79C at an angle, e.g., 2.5 degrees, relative to the inner guidance slots to form angled cuts into the underlying donor bone such that the resected graft may be formed with tapered sides for the press-fit implantation into the patient. Any of the template assemblies may be formed to have every resected side tapered. Alternatively, one or more sides of the resected graft may be selectively formed with a taper such that only one side is formed with the taper or two or more sides may be formed with the taper.

Figure 10A:
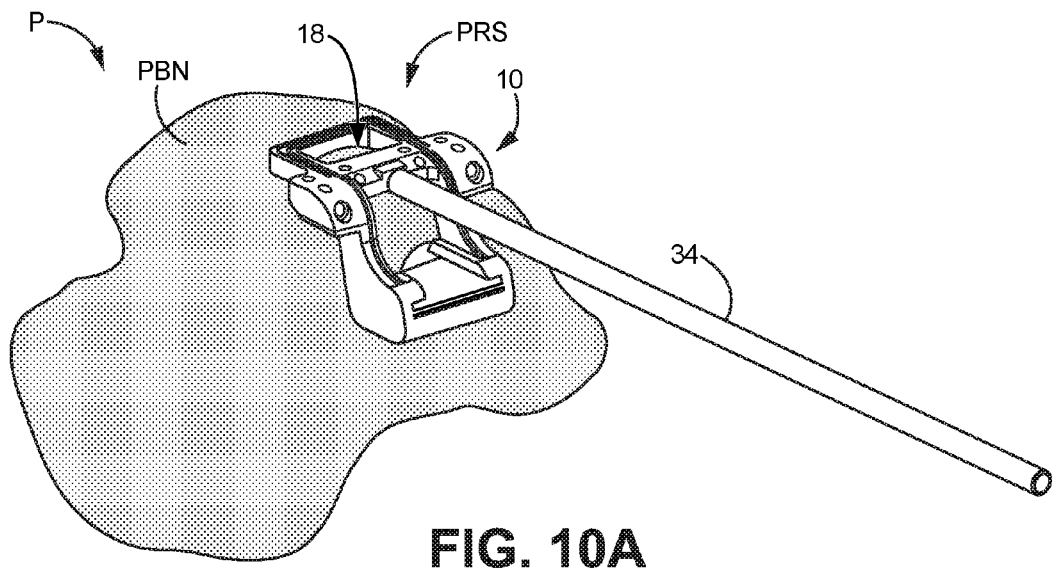
FIGS. 10A and 10B show perspective views illustrating a template placed upon a bone to be resected from a patient where portion of bone to be removed may be secured.
Figure 10B:
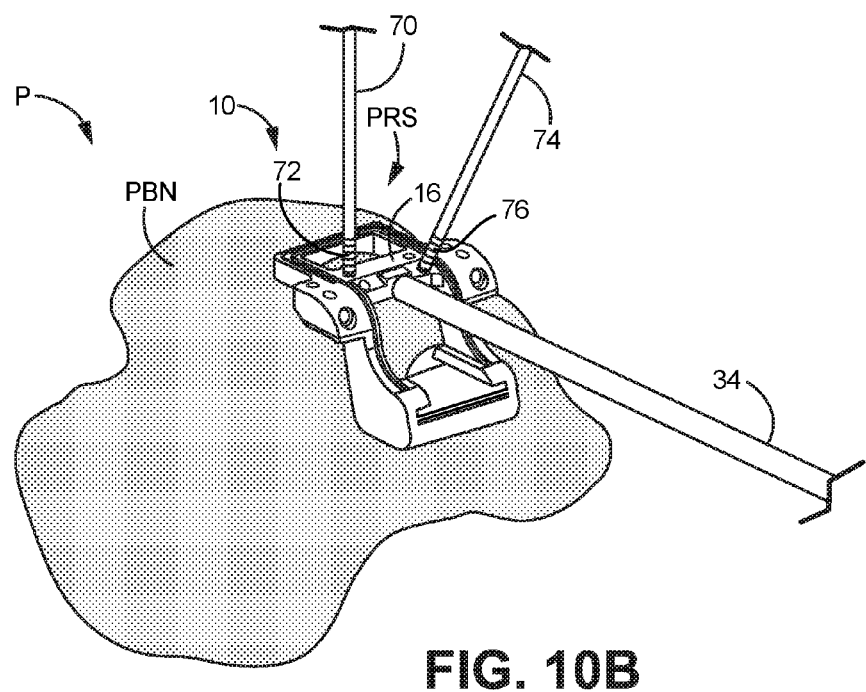

As shown in FIG. 10A, an example is illustrated where the bone of the patient P may be resected first. The portion of the bone to be repaired may be first identified and the template assembly 10 may then be placed into contact against the patient bone PBN such that the framed opening 18 of template assembly 10 surrounds the portion of the patient resected bone PRS to be repaired. With the template assembly 10 initially held in place against the surface of the patient bone PBN, e.g., via handle 34, one or more securement wires 70, 74 may be inserted through the template assembly 10, e.g., through the openings defined along cross-member 16, while monitoring their insertion depth to hold the template 10 in place relative to the bone surface, as shown in FIG. 10B. Because the damaged patient resected bone PRS bounded by framed opening 18 is to be removed from the patient bone PBN, the one or more securement wires 70, 74 may be inserted specifically into the patient resected bone PRS through cross-member 16 such that the surrounding bone may remain undamaged or untouched by the securement wires.

Figure 10C:
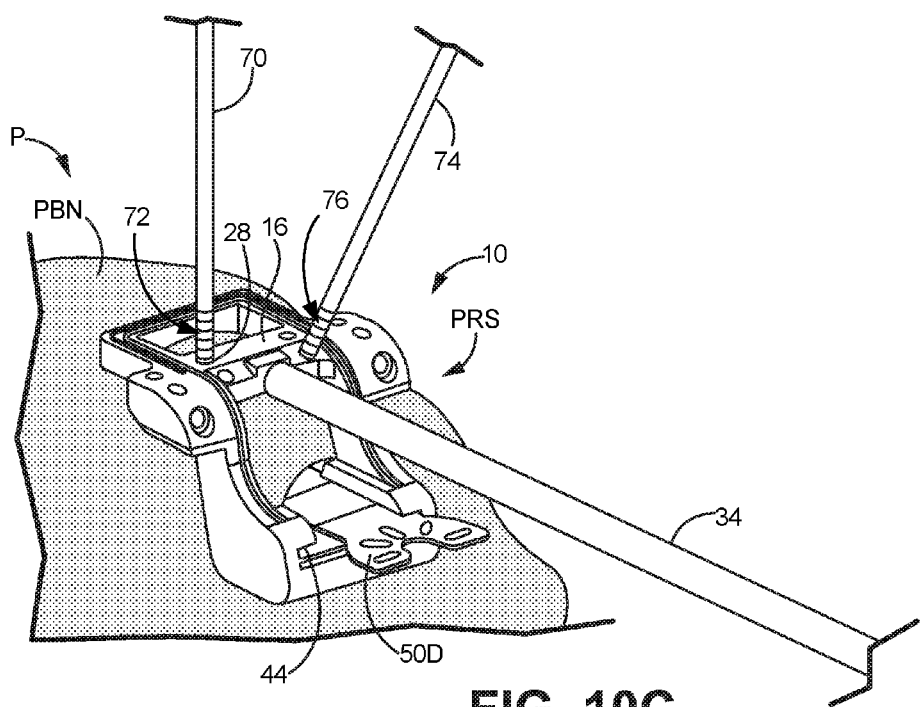
FIGS. 10C and 10D show perspective views illustrating the patient bone to be resected being sawed along the inner guidance slots.
Figure 10D:
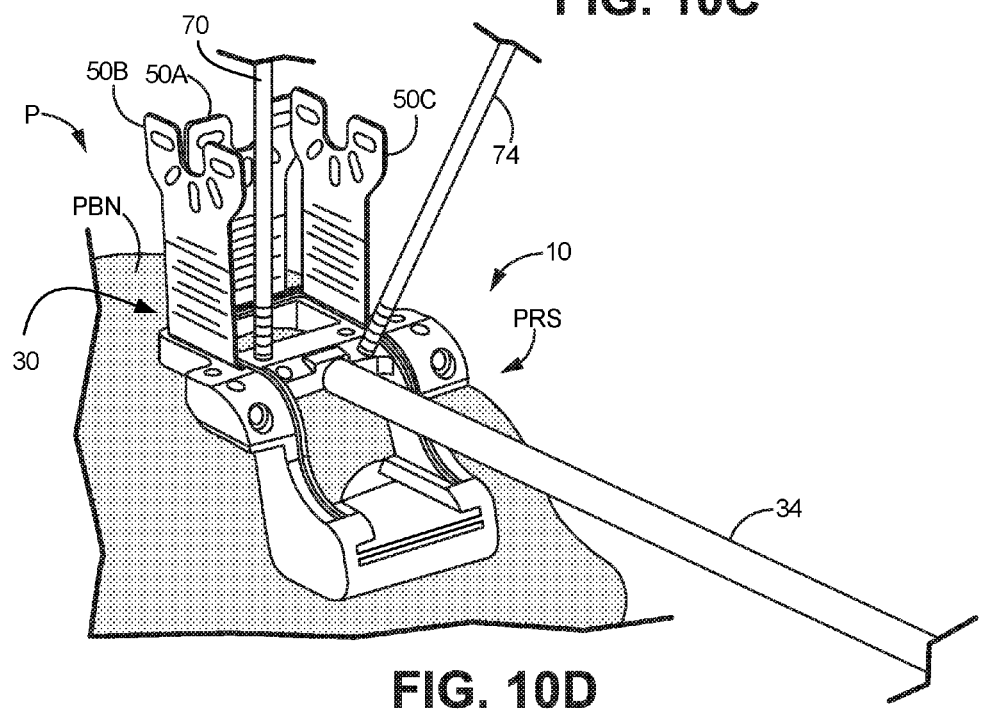

With the template assembly secured in place, the saw 50D may be inserted through inner guidance slot 44, as shown in FIG. 10C, and the bottom cut may be made into the bone first while monitoring and/or measuring the cutting depth via the optional graduations along the saw 50D. The saw 50D may be optionally left in place within the bone and the remaining cuts may then be made. Alternatively, the same saw 50D and/or additional saws, e.g., saws 50A, 50B, 50C, may be then inserted along the side inner guidance slots 40B, 40C to make the cuts into the patient bone PBN while monitoring and/or measuring the cutting depth. The same saw or additional saws may then be used to make the final cut along the distal inner guidance slot 40A, as shown in FIG. 10D. The patient resected bone PRS may be removed by tensioning the handle 34 and/or securement wires 70, 74 to leave the resected channel for grafting. In other variations, the order of the cuts into the bone may be altered as suitable or desired. For instance, the initial cut into the bottom of the patient resected bone PRS may be followed by cuts into the distal end of the bone followed by subsequent cuts along the sides of the bone. In yet other alternatives, an initial cut may be made along the distal end of the patient resected bone PRS followed by cuts along the bottom and/or sides of the bone.

Figure 11A:
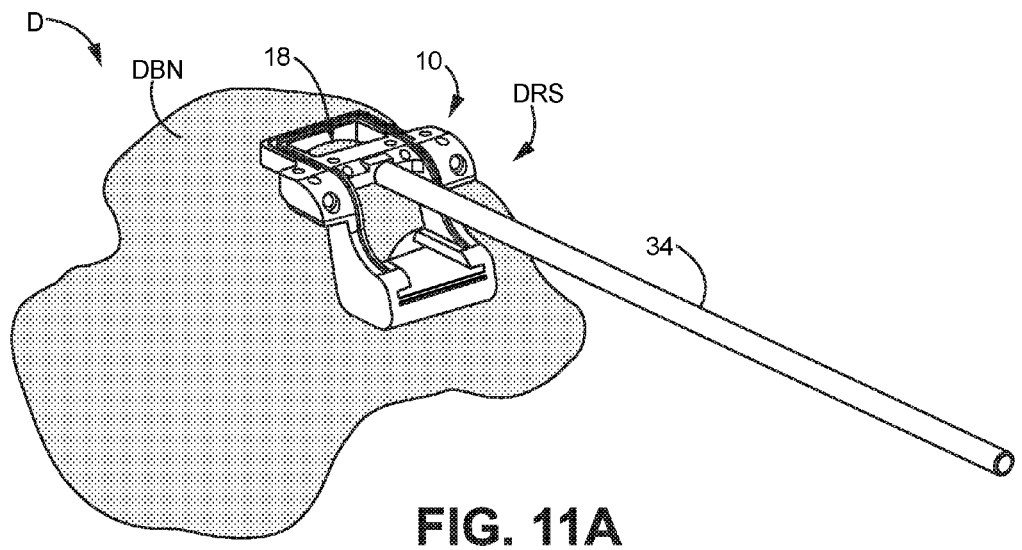
FIGS. 11A and 11B show perspective views illustrating the template secured to the bone of a donor outside of the portion to be resected.
Figure 11B:
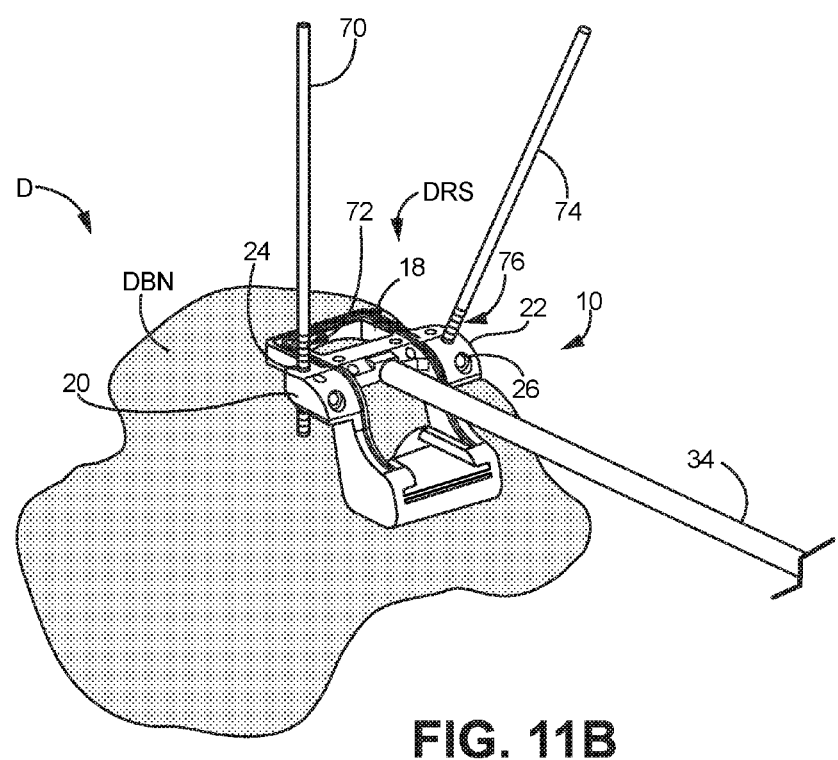

The patient resected bone PRS may be removed from the template assembly 10 which may then be placed into contact against the donor bone DBN from a donor D such that the framed opening 18 of template 10 bounds a region of the donor resected bone DRS, as shown in FIG. 11A, similar to the patient resected bone PRS. With the handle 34 used to hold the template 10 in place, one or more securement wires 70, 74 may then be passed through the openings 24, 26 defined along the supporting flanges 20, 22 which extend exteriorly of the framed opening 18 and into the underlying donor bone DBN while optionally measuring the insertion depth of the securement wires 70, 74, as shown in FIG. 11B. Because the donor resected bone DRS is to be removed from the donor bone DBN and grafted into the resected channel defined by the patient resected bone PRS, the one or more securement wires 70, 74 may be inserted through the supporting flanges 20, 22 to secure the template assembly 10 relative to the donor bone DBN. This ensures that the graft donor resected bone DRS remains undamaged by any additional openings which may otherwise be created by the insertion of securement wires.

Figure 11C:
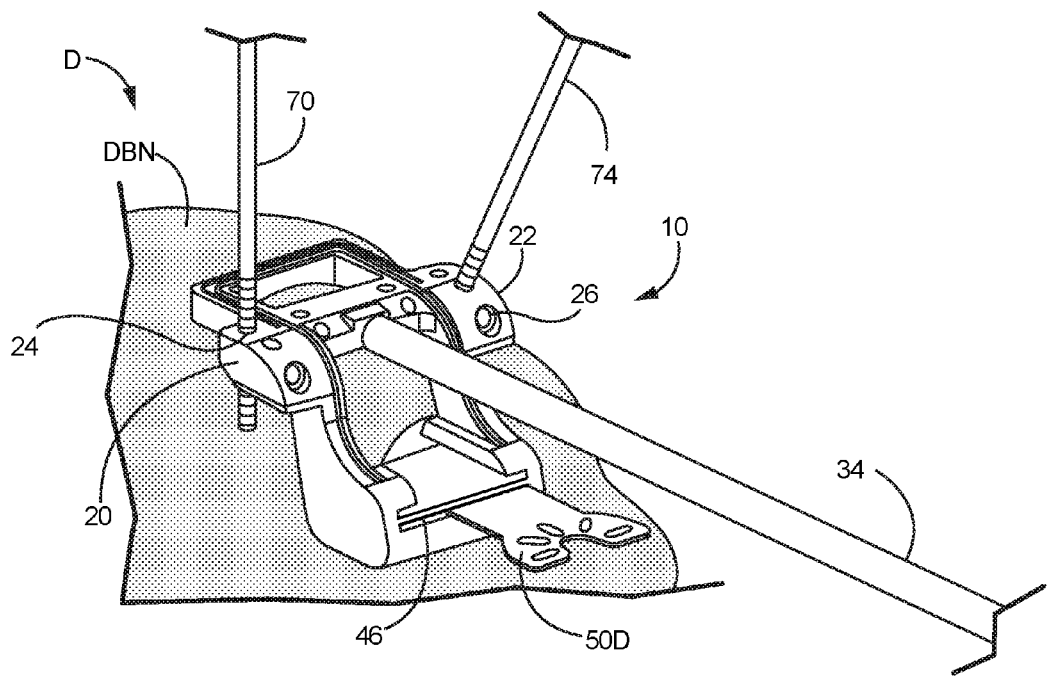
FIGS. 11C and 11D show perspective views illustrating the donor bone to be resected being sawed along the outer guidance slots.
Figure 11D:
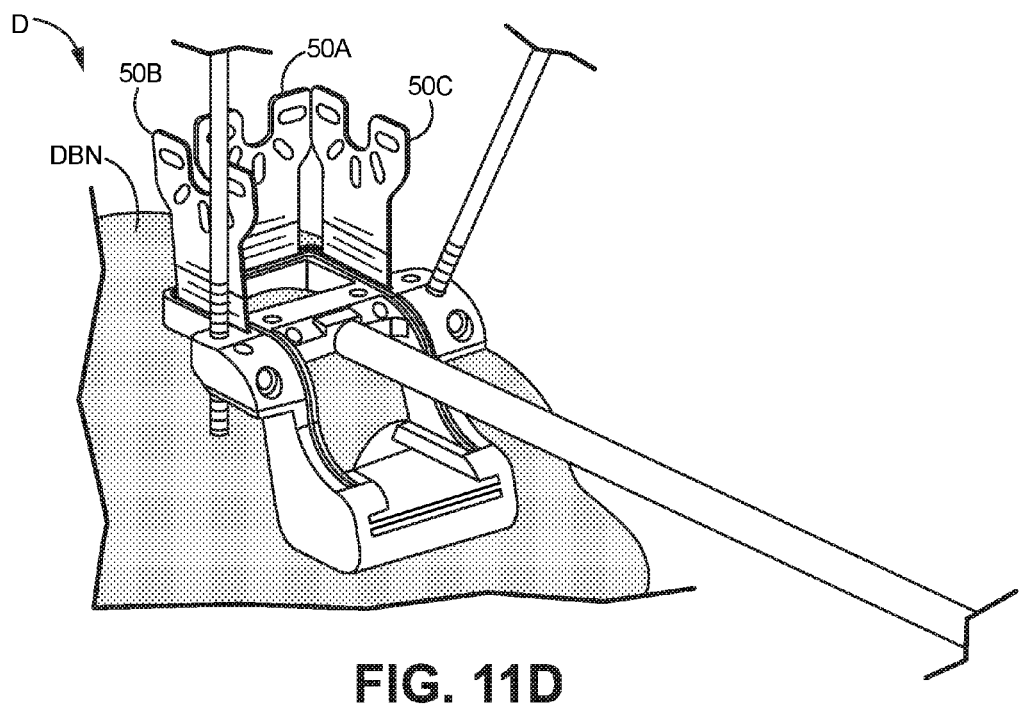

As illustrated in FIG. 11C, the bottom of the donor resected bone DBN may be cut by the insertion of saw 50D in a manner similar to the cutting of the patient resected bone PBN. However, the saw 50D may be inserted into and through the outer guidance slot 46 rather than the inner guidance slot 44. The depth of the cut may be monitored and/or measured by the graduations defined along the saw body, as previously described. The saw 50D or additional saws may then be used to form the cuts along the sides of the donor resected bone DBN by inserting the saws along the outer guidance slots 42B, 42C and the distal cut may also be made by inserting the saw along the outer guidance slot 42A, as shown in FIG. 11D. Once fully cut, the template assembly 10 may be removed from the donor bone DBN and the donor resected bone DBN may then be removed from the donor bone DBN and grafted into a press-fit into the channel defined by the patient resected bone PBN. As described above with respect to the cutting of the patient resected bone PBN, the donor resected bone DBN may be cut in differing order in alternative variations.

To provide for further flexibility in accommodating various anatomies and variances between patients and/or grafts, an allograft template assembly may be configured to have an adjustable medial offset which can be contoured or otherwise adjusted, e.g., to a talus dome or other transplate surface. Another variation of template is shown in the perspective view of FIG. 12 which illustrates an allograft template assembly 91 which is configured similarly to other variations described. In this particular embodiment, the template assembly 91 may incorporate a frame assembly 93A and curved portion 93B which is slidably adjustable relative to the rest of the assembly.

Figure 12:
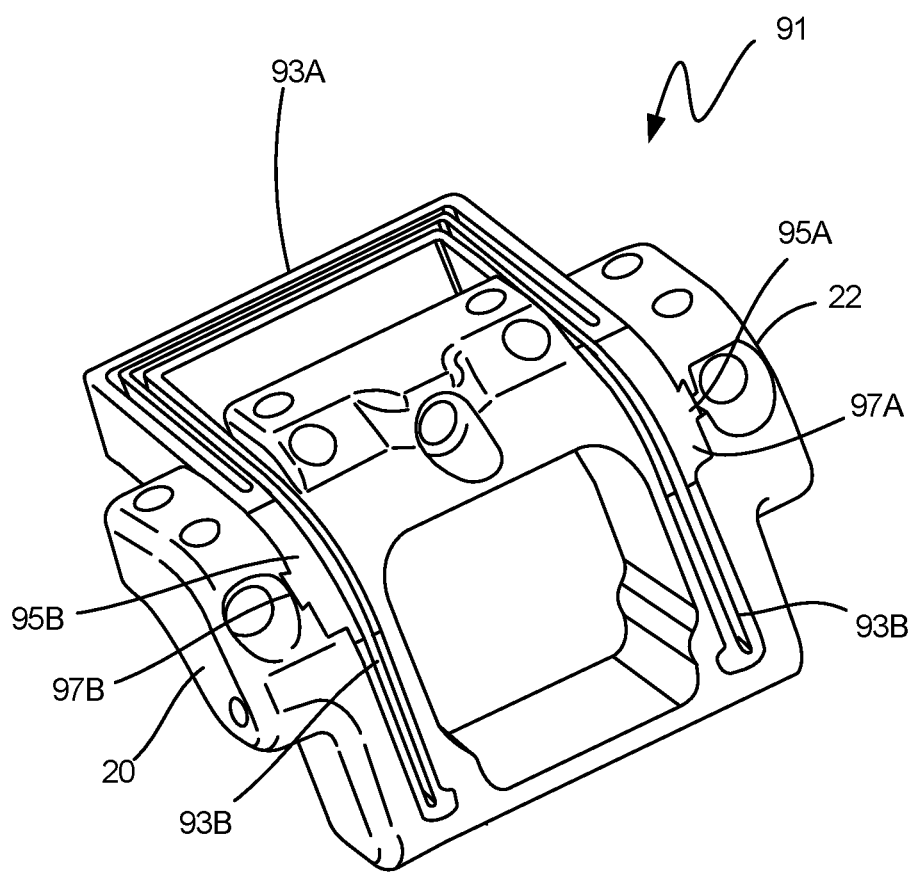
FIG. 12 shows a perspective view of another variation of an allograft template having an adjustable frame assembly.
Figure 13A:
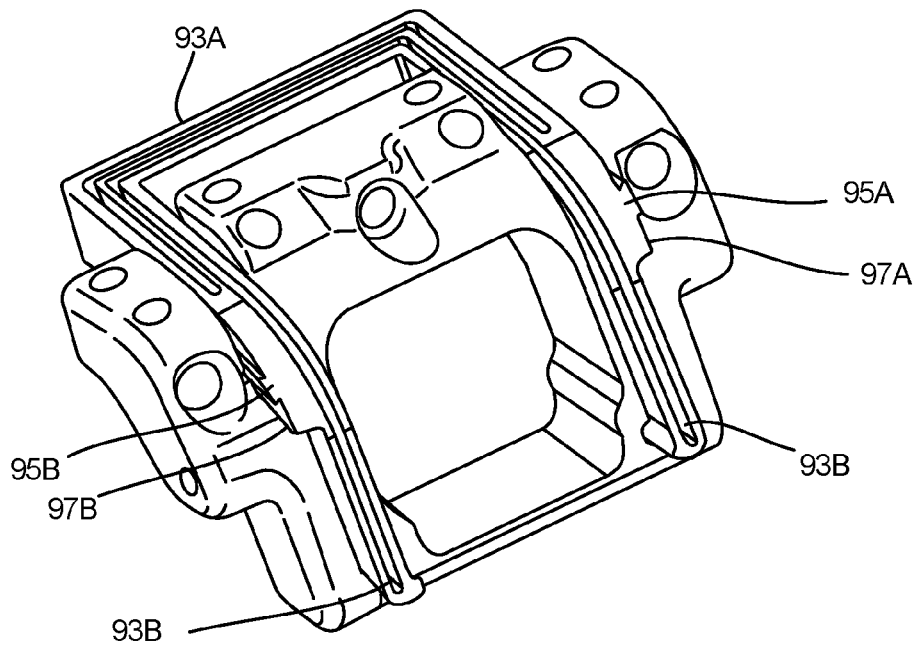
FIGS. 13A and 13B show perspective views of the adjustable allograft template illustrating the frame assembly adjusted into different configurations.
Figure 13B:
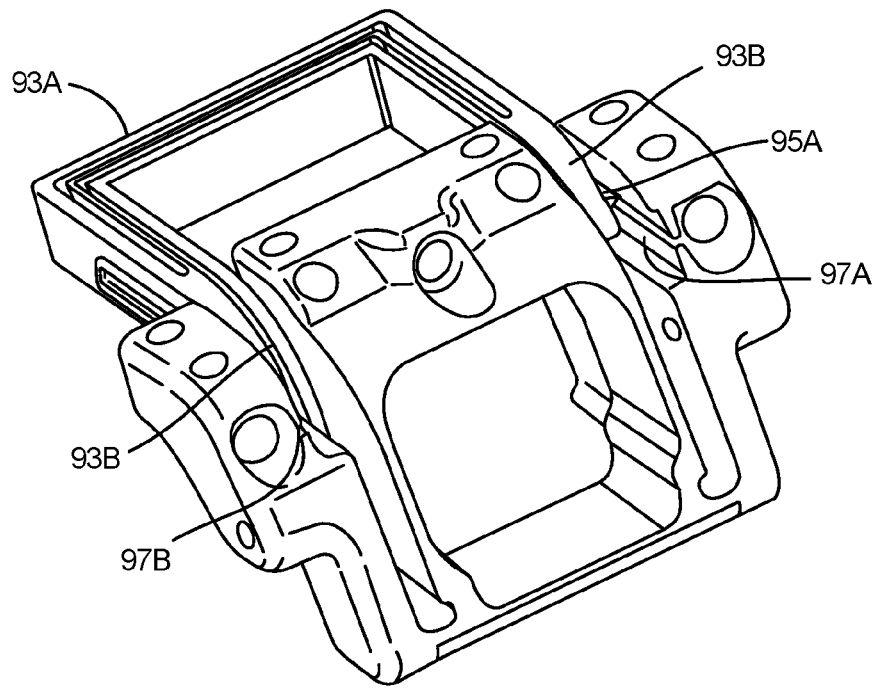

The frame assembly 93A may translate proximally or distally along guides 95A, 95B along respective channels 97A, 97B in-between supporting flanges 20, 22. The variation shown in FIG. 12 illustrates the frame assembly 93A aligned at a nominal position relative to the assembly such that the surfaces remain flush as in the previous variations. However, FIGS. 13A and 13B illustrate how the frame assembly 93A may be translated to various depths. FIG. 13A shows a perspective view of the frame assembly 93A advanced proximally relative to the assembly such that the amount of the patient bone or graft bone may be reduced in depth during a resection procedure. As shown, as the frame assembly 93A is translated, the curved portion 93B may be corresponding translated as well such that the depth of the resected bone remains consistent.

FIG. 13B likewise shows a perspective view of the template assembly but where the frame assembly 93A and curved portion 93B has been adjusted to a distal position relative to the assembly. In this case, the depth of the patient bone or graft bone may be increased correspondingly depending upon the patient anatomy and desired amount of bone to be resected. To assist in adjusting the depth of the assembly, indicators or gradations may be defined along the assembly 91 to facilitate positioning of the adjusted depth. Alternatively, the depth of the frame assembly 93A and curved portion 93B may be adjusted directly against the patient bone and frame assembly 93A may be locked into position to maintain the consistency with the donor graft as well.

Regardless of the depth of the translated frame assembly 93A and curved portion 93B, the amount of bone resected from the patient and graft may be maintained in a consistent manner by locking the frame assembly 93A and curved portion 93B not only to the underlying bone but also relative to the assembly 91 as well to prevent undesired movement during resection. Moreover, regardless of the positioning of the frame, the resection procedure may be carried out in the same or similar manner as described herein.

Figure 14A:
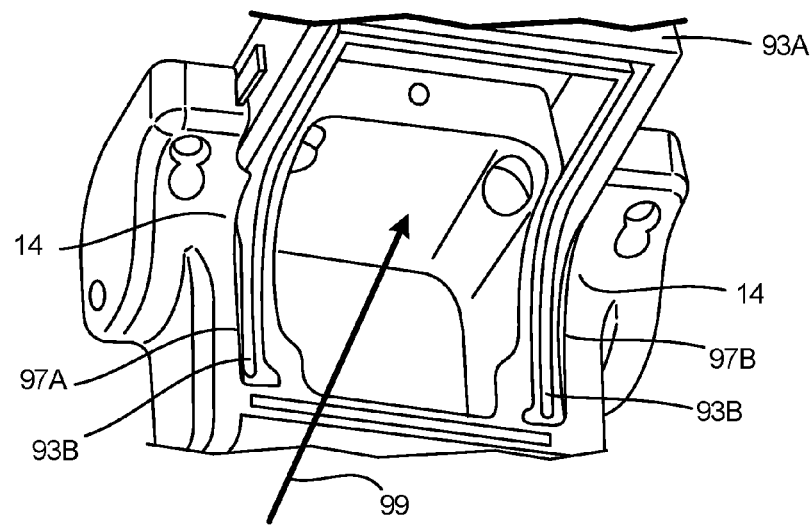
FIGS. 14A and 14B show perspective views illustrating how the adjustable allograft template may be adjusted to vary the template position relative to the underlying bone.

As shown in the perspective view of FIG. 14A, the contact surface 14 is illustrated to show how the depth of the frame assembly 93A may be adjusted by, e.g., translating the frame assembly 93A along the direction of the movement 99. Alternatively, the contact surface 14 may be adjusted to match to a bone topography, e.g., obtained through a CT scan, by varying the frame assembly 93A positioning relative to the assembly 91 and locking the position of the frame assembly 93A.

Figure 14B:
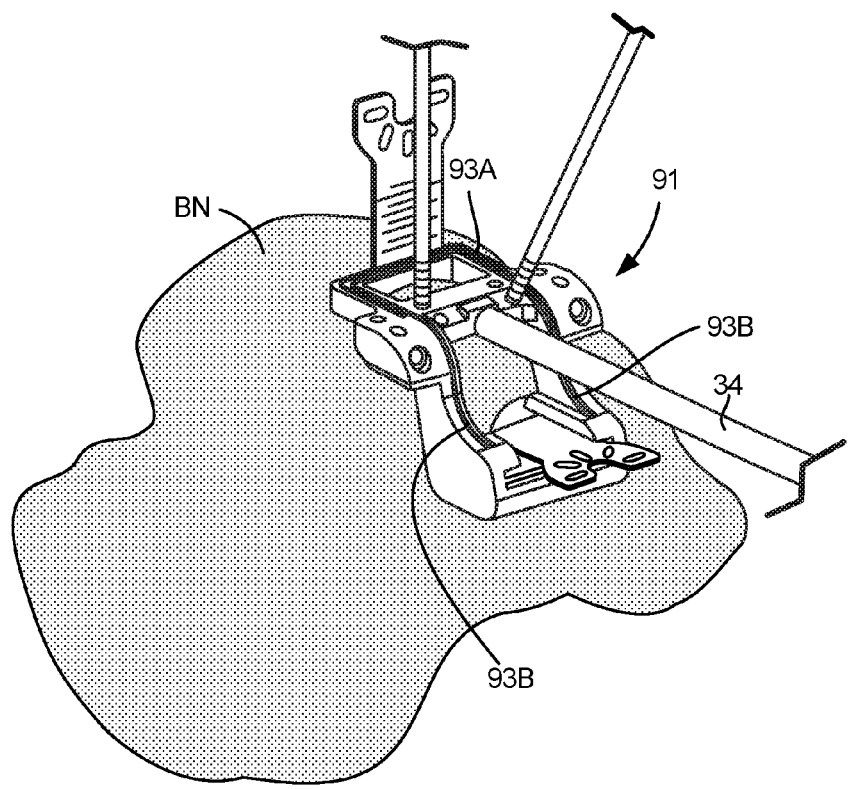

FIG. 14B shows a perspective view of how the adjustable template assembly 91 may be positioned upon a region of the bone BN to be resected. Once the frame assembly has been suitably adjusted, it may also be stabilized on the bone surface with, e.g., one or more K-wires, as previously described.

Figure 15:
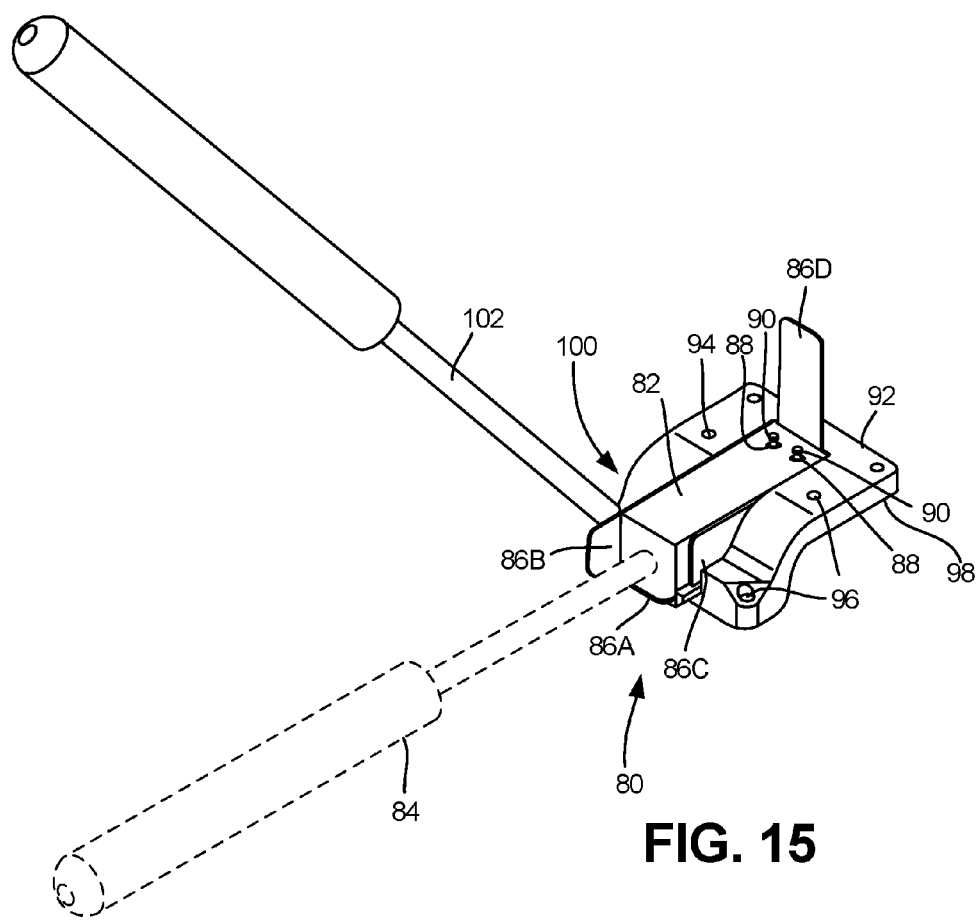
FIG. 15 shows a perspective view of another variation of an allograft template.

In yet another variation of the template assembly, FIG. 15 shows a template which may utilize a template for placement upon a bone of the donor and an additional template for placement upon a bone of the patient. A common guide housing may be utilized between the two different templates to maintain consistency between the resected bone from the patient and the resected bone from the donor for grafting into the patient bone.

As shown in the perspective view of FIG. 15, an internal saw guide assembly 80 may be seen which may utilize a guide housing 82 between the bone of the patient and the bone of the donor to maintain cutting consistency. The guide housing 82 may form a housing which is open along the portion which contacts the surface of the bone (both donor and patient) to be resected. The guide housing 82 may have a handle 84 which extends from the housing 82 and may further define channels along the sides and bottom portion of the housing for guiding and/or receiving one or more saws 86A, 86B, 86C, 86D. The top of the guide housing 82 may define one or more openings 88 through which one or more corresponding securement wires or pins 90, as above, may be inserted for securing the guide housing 82 to the underlying bone.

The guide housing 82 may be engaged with or inserted along a donor template 92, as shown, as well as a corresponding patient template, as described below. The donor template 92 may define one or more openings 94, 96 through which securement wires or pins may be inserted for securing the template 92 to the donor bone. The donor template 92 may accordingly define a contact surface 98 for placement along or upon the underlying bone as a well as a curved template portion 100 to facilitate conformance against the bone surface. A handle 102 may also extend from the donor template 92 to facilitate handling of the assembly.

Figure 16A:
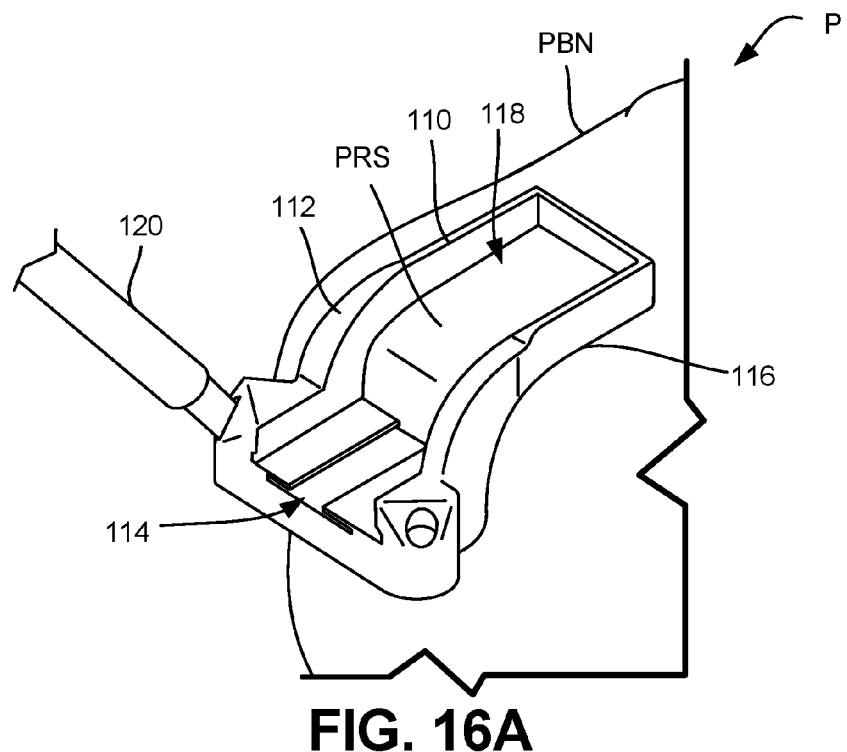
FIGS. 16A and 16B show perspective views illustrating a patient template secured to the bone of the patient.
Figure 16B:
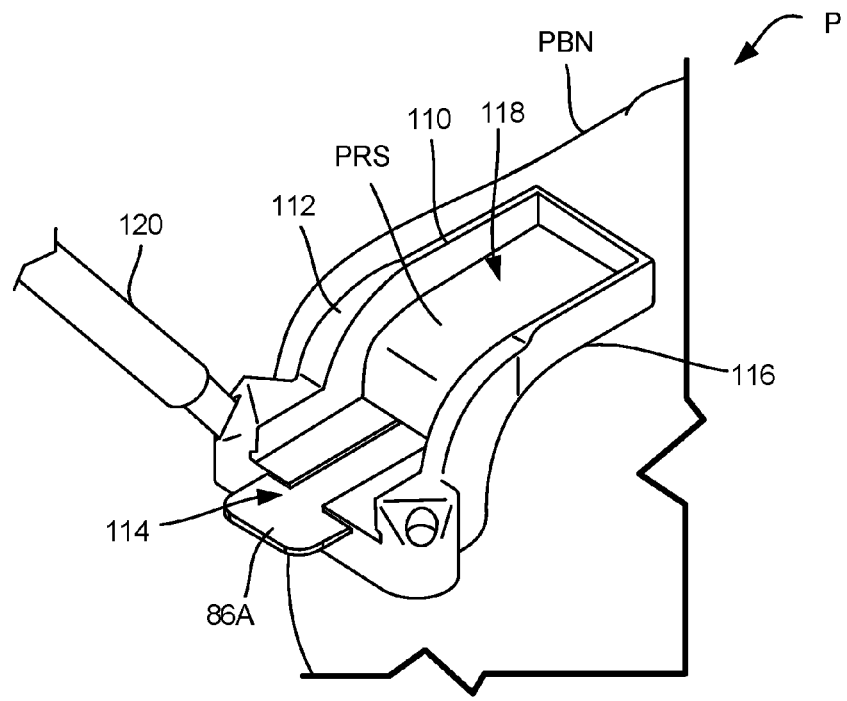
Figure 16C:
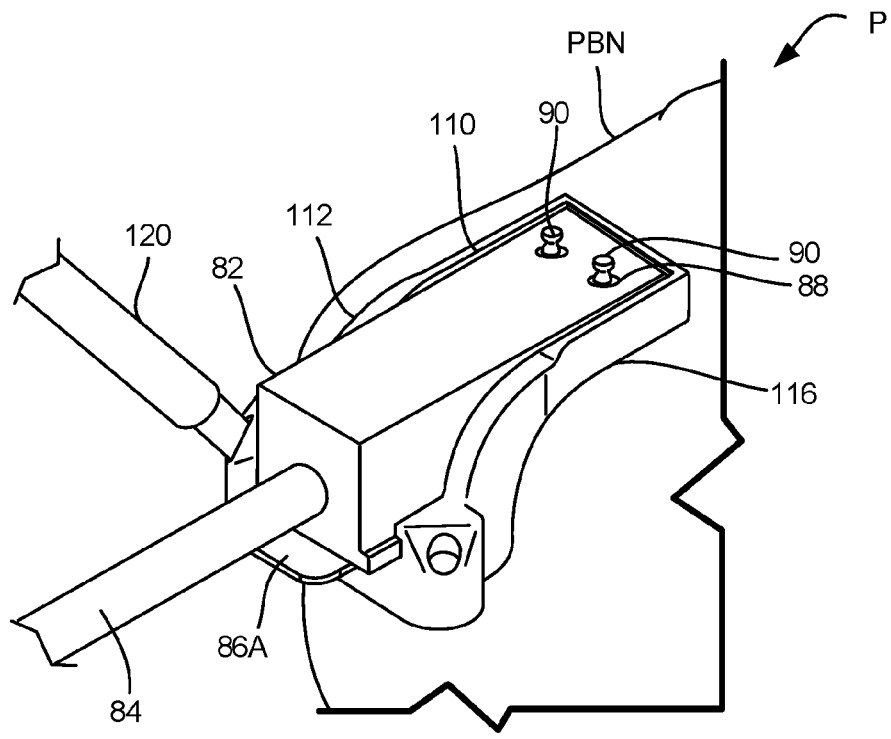
FIGS. 16C and 16D show perspective views illustrating a guide housing being secured along the patient template and the patient bone sawed accordingly.

In use, a patient template 110 which defines a curved template portion 112 and a contact surface 116 for conformance against the underlying patient bone PBN may be placed upon a region of the patient bone PBN such that the framed opening 118 bounds the portion of the patient resected bone PRS which is damaged and which is to be replaced by a graft, as shown in the perspective view of FIG. 16A. The patient template 110 may be maintained in place against the patient bone PBN by the handle 120 attached to the template 110 and/or by one or more securement wires which may be inserted through the template 110 and into the underlying bone, as described previously. A first saw 86A may be inserted through a saw guide 114 defined along the template 110 to a predetermined depth, as shown in FIG. 16B. Then the guide housing 82 may be advanced along and within the framed opening 118 such that the guide housing 82 is fully engaged within the template 110. The guide housing 82 may be secured and maintained against the patient template 110 as well as the patient bone PBN by inserting one or more securement wires or pins 90 through the openings 88 defined through the guide housing 82, as shown in FIG. 16C. As previously described, the securement wires or pins 90 may be secured directly to the patient respected bone PRS to be removed and replaced by the graft.

Figure 16D:
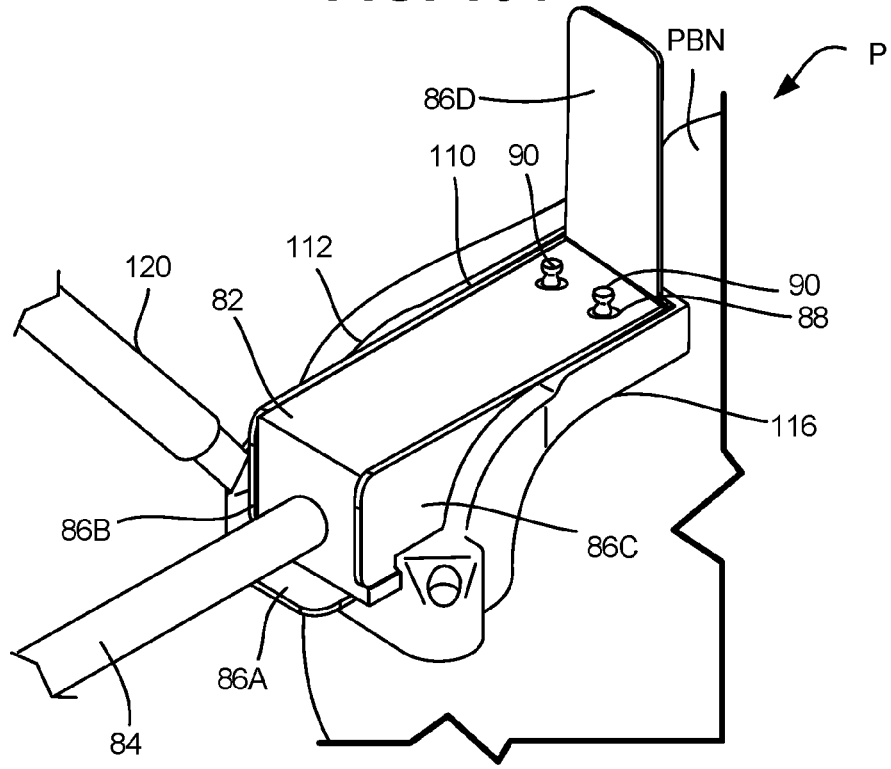

With the guide housing 82 secured within the patient template 110 and against the patient resected bone PRS, a second saw 86D may be inserted between the patient template 110 and the distal portion of the guide housing 82, as shown in FIG. 16D. The saw 86D may be inserted to a predetermined depth, e.g., by one or more graduations defined along the saw body, or until the distal cutting edge comes into contact against the first saw 86A which may be left in place within the bone to define a stop or boundary to prevent the further advancement of saw 86D into the underlying patient bone PBN. The remaining saws 86B, 86C may be advanced along the sides of the guide housing 82 and within patient template 110 to completely resect the patient resected bone PRS within the guide housing 82.

Figure 17A:
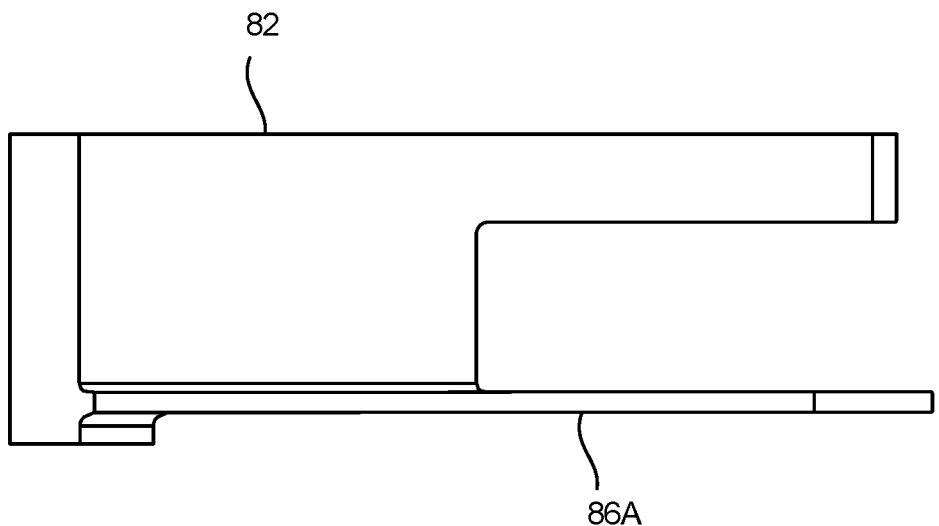
FIGS. 17A and 17B show side and bottom views of a variation of a guide housing used for guiding the saw blades.
Figure 17B:
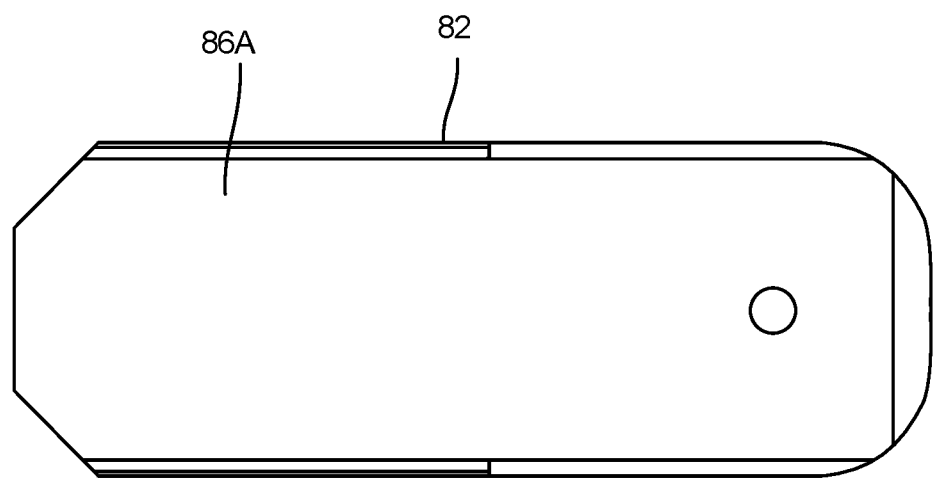

FIGS. 17A and 17B show side and bottom views of another variation of the guide housing 82 to illustrate the opening defined by the housing 82 for contact against the underlying bone. The first saw 86A may be seen advanced along the guide housing 82 to form a bottom surface of the guide housing 82 as well as to form a backstop against which the remaining saws may be advanced or guided along or against to maintain a controlled cutting path through the bone.

Figure 18A:
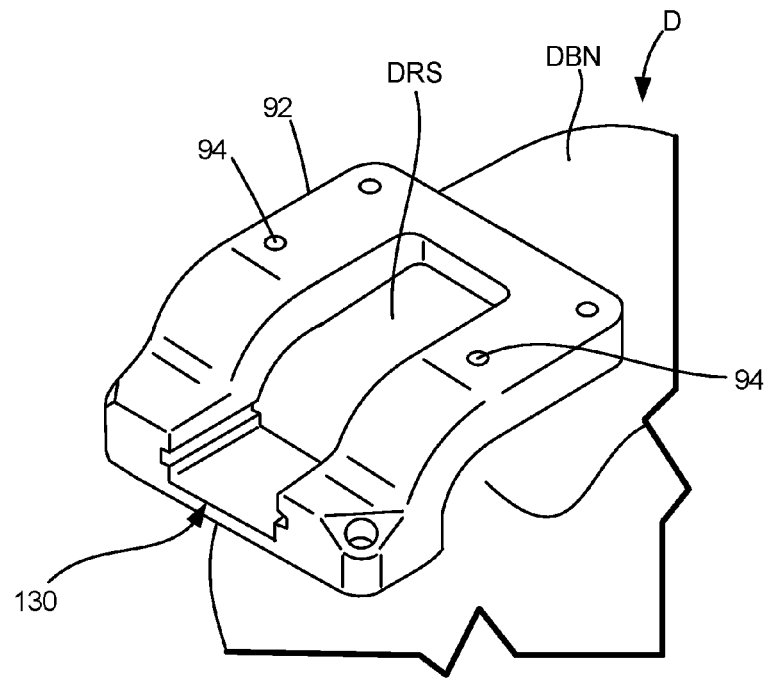
FIGS. 18A and 18B show perspective views of a donor template secured to the bone of the donor and the guide housing secured along the template.
Figure 18B:
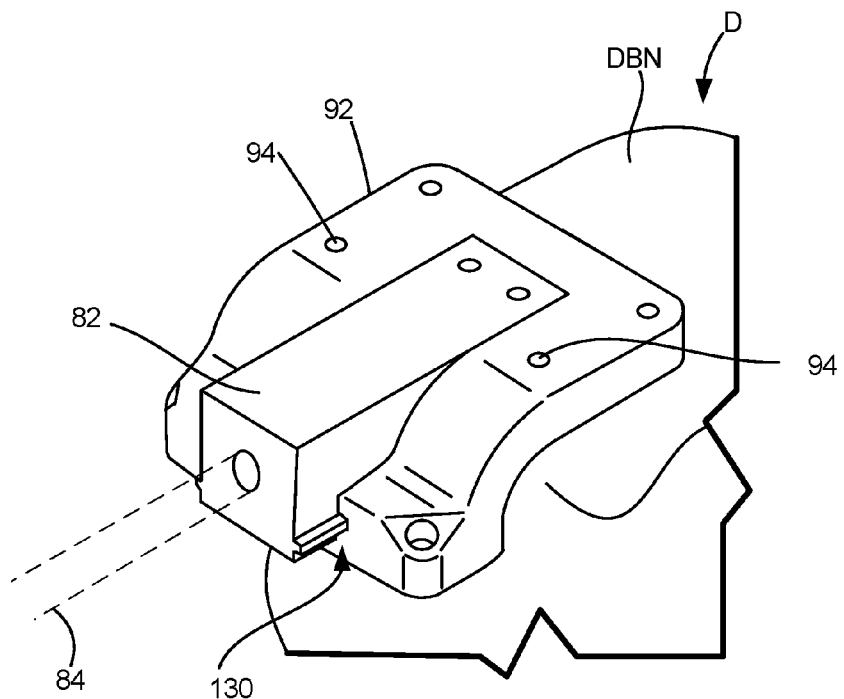

With the patient bone resected, the donor bone may also be resected in a similar manner but with a second donor template 92 which defines an opening which corresponds in size with the patient template framed opening 118. The donor template 92 may similarly define a contact surface for placement against the donor bone DBN such that the opening of the donor template 92 frames the donor resected bone DRS to be grafted, as shown in the perspective view of FIG. 18A. Hence, the framed donor resected bone DRS may be consistent in size with the channel defined by the patient resected bone PRS in the patient bone PBN. The donor template 92 similarly defines one or more openings 94 through which the securement wires or pins may be inserted away from the donor resected bone DRS, as described above, to maintain the integrity of the graft. The donor template 92 may define a receiving channel 130 along the template for receiving the guide housing 82 in a consistent orientation, as shown in FIG. 18B. Hence, the same guide housing 82 used to create the patient resected bone PRS may be advanced into a sliding engagement optionally through receiving channel 130 upon the donor bone DBN.

Figure 18C:
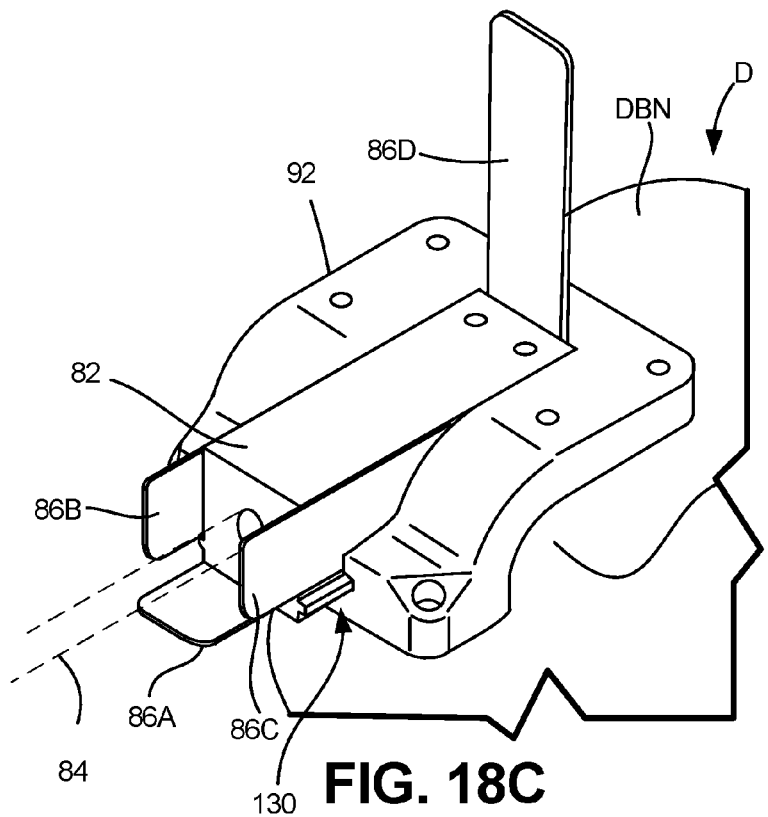
FIGS. 18C and 18D show perspective views of the donor bone being resected by the saw blades.
Figure 18D:
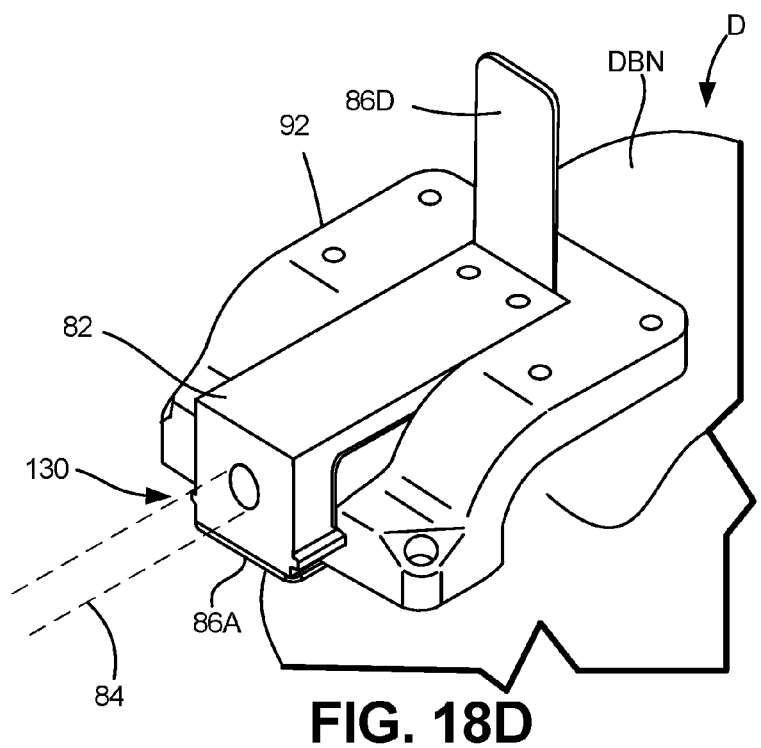

As with resection of the patient bone PBN, once the guide housing 82 is secured along the donor template 92, the first saw 86A may be advanced along the bottom portion of the donor resected bone DRS, as shown in FIG. 18C. The additional saws 86D may be advanced into contact against the first saw 86A to form the distal end of the donor resected bone DRS and the remaining saws 86B, 86C may be advanced along the respective sides of the guide housing 82 between the donor template 92 to completely resect the donor resected bone DRS within the guide housing 82, as shown in FIG. 18D. The donor resected bone DRS may then be removed from the donor bone DBN and grafted into the channel formed by the patient resected bone PRS.

Figure 19A:
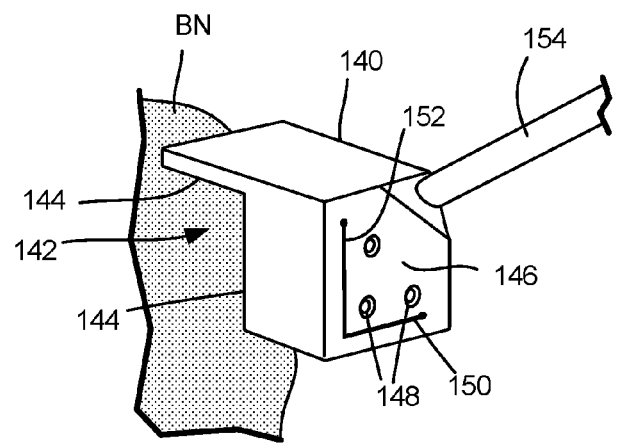
FIGS. 19A to 19C show various perspective views of another variation of an allograft template which allows for bone resection along an anterior or side portion of the bone.
Figure 19B:
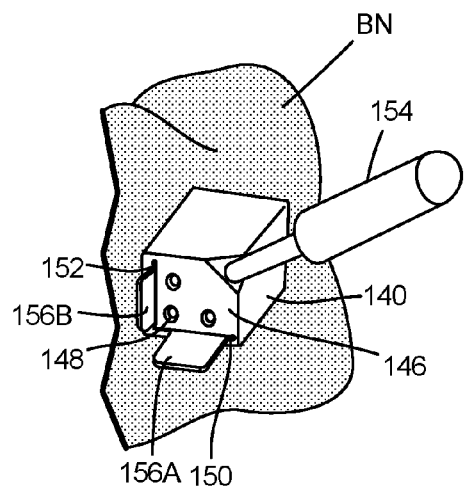
Figure 19C:
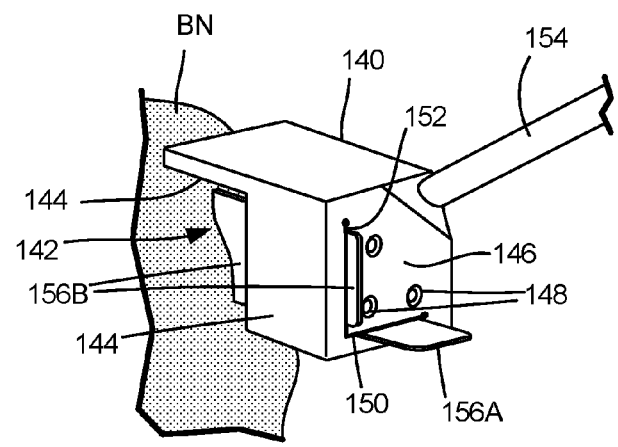

In yet another variation of a resection template, FIGS. 19A to 19C show various perspective views of a guide template 140 which is configured to be placed against an anterior portion of a bone to be resected. The anterior guide template 140 may be configured to form a bone receiving channel 142 defined by contact surfaces 144 formed along template walls extending partially from a transversely oriented guide surface 146. A handle 154 may extend from the anterior guide template 140 to facilitate handling of the template and the guide surface 146 may define one or more openings 148 for the passage of securement wires or pins into the underlying bone to be resected. The guide surface 146 may also define one or more guidance slots 150, 152 which may be aligned in a transverse orientation such that one or more corresponding saws 156A, 156B may be inserted into the respective slots to cut the bone contained within the bone receiving channel 142.

Figure 20A:
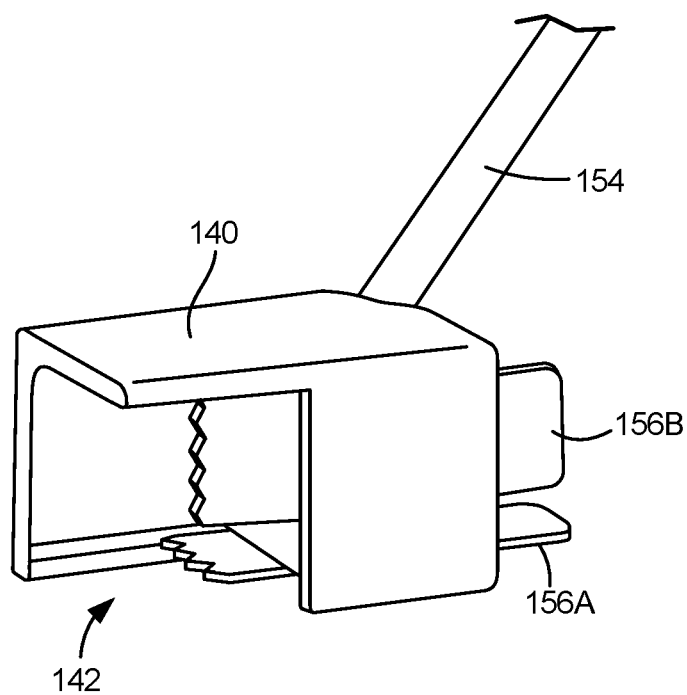
FIGS. 20A and 20B show perspective and end views of the allograft template.
Figure 20B:
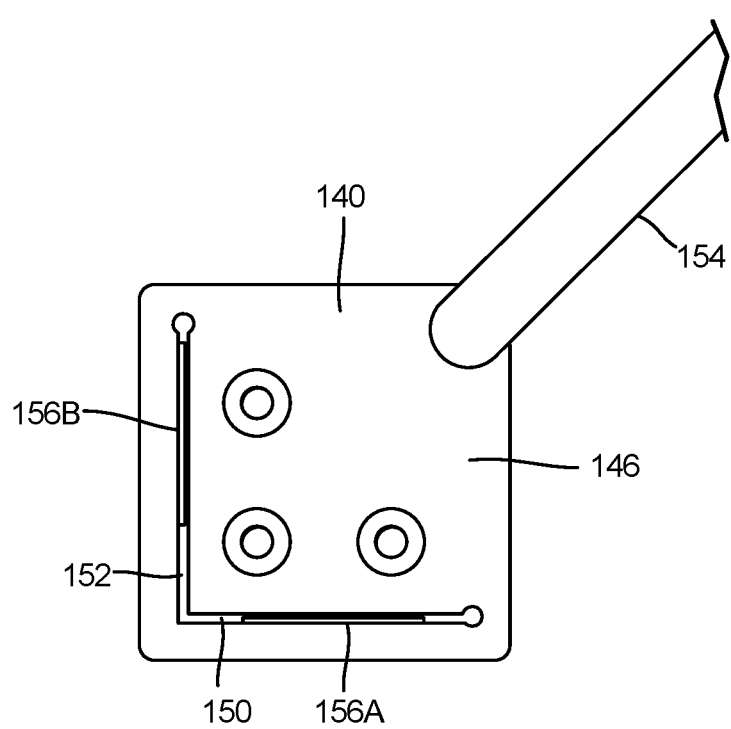

FIGS. 20A and 20B show alternate perspective and end views of the anterior guide template 140 to illustrate how the saws 156A, 156B may be inserted through the respective guidance slots 150, 152 in a linear manner such that when advanced, the resected bone may be contained within the bone receiving channel 142 with consistent cuts along the resected portions. The anterior guide template 140 may be used to resect not only the donor bone but also the patient bone to ensure that the resected channel in the patient bone is consistent with the resected bone graft from the donor.

Figure 21A:
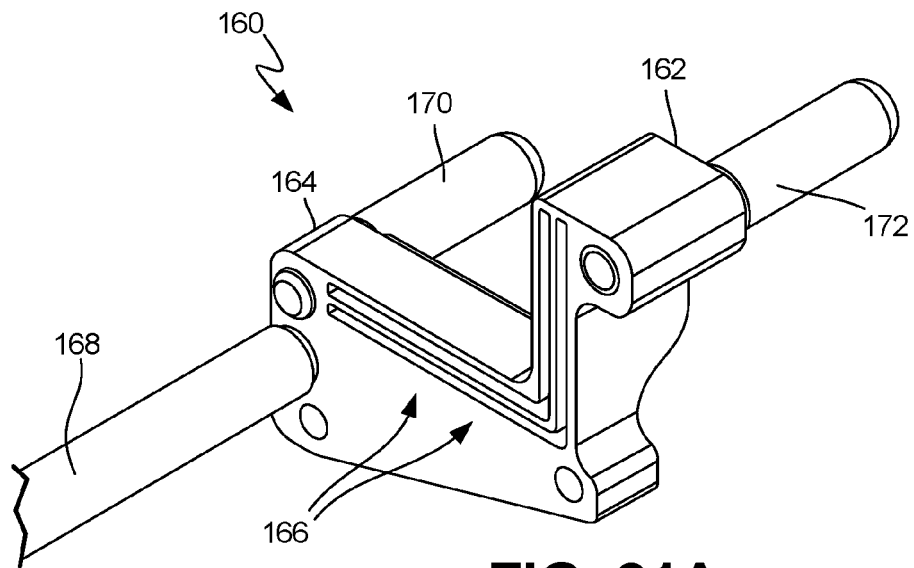
FIGS. 21A and 21B show perspective and end views of another variation of an allograft template.
Figure 21B:
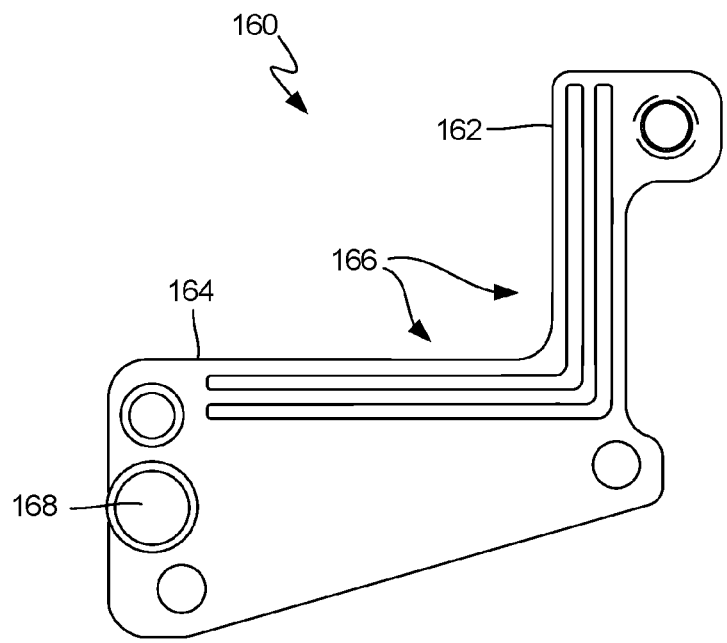

In yet another variation, FIGS. 21A and 21B show perspective and end views of another anterior template assembly 160 which may be comprised generally of a first guide section 162 and a second guide section 164 which are transversely oriented relative to one another. A handle 168 may extend from the first or second guide section 162, 164 which may optionally incorporate one or more guide pins 170, 172. The first and second guide sections 162, 164 may define parallel inner and outer guidance slots 166 for the insertion of saws for resecting bone segments from the patient bone and the donor bone while utilizing the same anterior template assembly 160. The use of the offset guidance slots 166 may allow for the creation a donor resected bone which is slightly larger than the resection channel formed in the patient bone to ensure a press-fit graft, as described above.

Figure 22A:
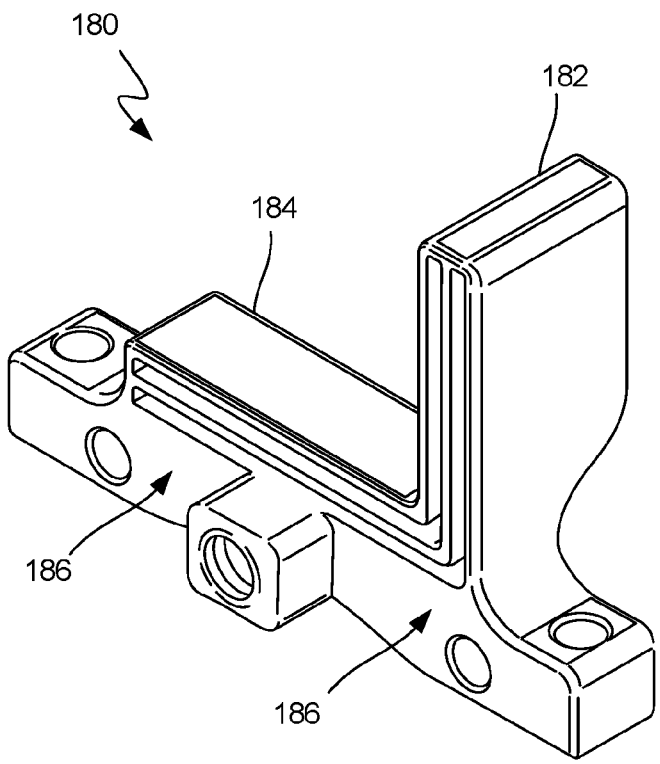
FIGS. 22A and 22B show perspective and end views of yet another variation of an allograft template.
Figure 22B:
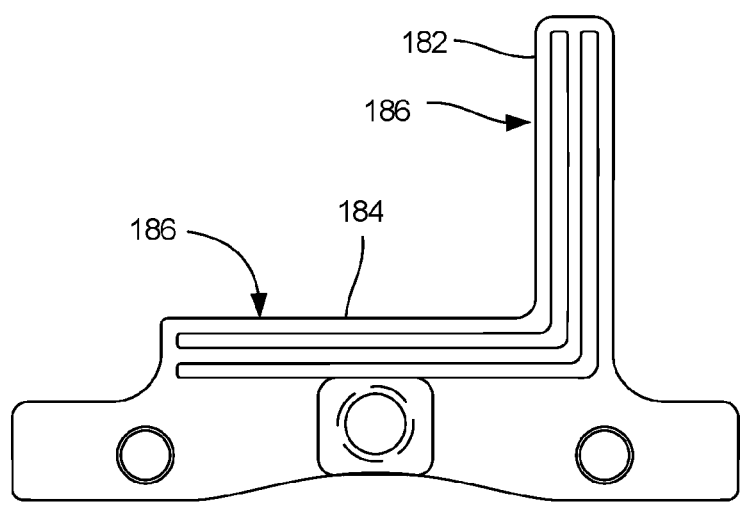

Another variation is shown in the perspective and end views of FIGS. 22A and 22B of an anterior template assembly 180 similarly having a first guide section 182 and a transversely oriented second guide section 184. As with the embodiment of FIGS. 21A and 21B, the first and second guide sections 182, 184 may define parallel inner and outer guidance slots 186 for resecting bone segments from both the patient bone and donor bone.

The applications of the devices and methods discussed above are not limited to bone resection along the talus bone but may include any number of other bones or tissue regions in the body. Modification of the above-described assemblies and methods for carrying out the invention, combinations between different variations as practicable, and variations of aspects of the invention that are obvious to those of skill in the art are intended to be within the scope of the claims.

What is claimed is:

1. A template for resecting a tissue region, comprising:
   (a) a template assembly having a curved surface for contacting the tissue region;
   (b) a frame assembly comprising:
      (i) first and second inner guidance slots defined along the frame assembly, wherein the first and second inner guidance slots are spaced relative to one another to define a width of tissue to be resected from a patient;
      (ii) a third inner guidance slot defined along the frame assembly, wherein a length of the third inner guidance slot is perpendicular to a length of each of the first and second inner guidance slots and wherein the third inner guidance slot defines a length of the tissue to be resected from the patient;
      (iii) first and second outer guidance slots defined along the frame assembly and aligned adjacent to the first and second inner guidance slots, wherein the first and second outer guidance slots are positioned closer to an outer edge of the frame assembly in relation to the first and second inner guidance slots, wherein the first and second outer guidance slots are spaced relative to one another to define a width of tissue to be resected from a donor, wherein the width of tissue to be resected from the donor is greater than the width of tissue to be resected from the patient; and
      (iv) a third outer guidance slot defined along the frame assembly and aligned adjacent to the third inner guidance slot, wherein the third outer guidance slot is positioned closer to the outer edge of the frame assembly in relation to the third inner guidance slot, wherein a length of the third outer guidance slot is perpendicular to a length of each of the first and second outer guidance slots and wherein the third outer guidance slot defines a length of the tissue to be resected from the donor, wherein the frame assembly is translatable relative to the template assembly.

2. The template of claim 1, wherein the frame assembly comprises a first portion which lies along a first plane and a second curved portion which extends and curves in an arcuate manner away from the first portion along a second plane.

3. The template of claim 1 wherein the first, second, and third outer guidance slots are formed at an angle relative to the first, second, and third inner guidance slots along the frame.

4. The template of claim 3 wherein the angle of the first, second, and third outer guidance slots is 2.5 degrees relative to the first, second, and third inner guidance slots.

5. The template of claim 1 wherein a shape of the frame assembly is variable according to a shape of the tissue to be resected.

6. The template of claim 1 further comprising one or more saws which are insertable through the first, second, and third inner guidance slots and the first, second, and third outer guidance slots.

7. The template of claim 1 wherein the frame assembly defines one or more openings sized for a securement wire or pin.

8. The template of claim 7 further comprising one or more securement wires or pins for insertion through the one or more openings.

9. A template for resecting a tissue region, comprising:
(a) two channels defined in a template assembly;
(b) a curved contact surface defined in the template assembly; and
(c) a frame assembly slidably positioned within the two channels, the frame assembly comprising:
  (i) first, second, and third inner guidance slots defined in the frame assembly, wherein a length of the third inner guidance slot is perpendicular to a length of each of the first and second inner guidance slots, and wherein the first, second, and third inner guidance slots are defined in the frame assembly in relation to each other so as to define an area of tissue to be resected from a patient; and
  (ii) first, second, and third outer guidance slots defined in the frame assembly substantially adjacent to the first, second, and third inner guidance slots, respectively, wherein a length of the third outer guidance slot is perpendicular to a length of each of the first and second outer guidance slots, wherein the first, second, and third outer guidance slots are positioned closer to and substantially adjacent to an outer edge of the frame assembly in relation to the first, second, and third inner guidance slots, and wherein the first, second, and third outer guidance slots are defined in the frame assembly in relation to each other so as to define an area of tissue to be resected from a donor,
  wherein the frame assembly is slidable in relation to the template assembly such that a size of the area of tissue to be resected from the patient and a size of the area of tissue to be resected from the donor is adjustable.

10. The template of claim 9, wherein the size of the area of tissue to be resected from the donor is larger than the size of the area of tissue to be resected from the patient.

11. The template of claim 9, further comprising a fourth inner guidance slot defined in the template assembly.

12. The template of claim 11, further comprising a fourth outer guidance slot defined in the template assembly, wherein the fourth outer guidance slot is substantially adjacent to the fourth inner guidance slot.

13. The template assembly of claim 12, wherein a length of the fourth outer guidance slot is perpendicular to the length of each of the first and second outer guidance slots.

14. The template assembly of claim 12, wherein the first, second, third, and fourth outer guidance slots define the area of tissue to be resected from the donor.

15. The template assembly of claim 11, wherein a length of the fourth inner guidance slot is perpendicular to the length of each of the first and second inner guidance slots.

16. The template assembly of claim 11, wherein the first, second, third, and fourth inner guidance slots define the area of tissue to be resected from the patient.

17. A template for resecting tissue, the assembly comprising:
(a) first and second channels defined in a template assembly;
(b) a contact surface defined on a distal portion of the template assembly, the contact surface comprising a predefined concave curvature;
(c) a frame assembly slidably disposed within the first and second channels;
(d) first, second, and third inner guidance slots defined in the frame assembly, wherein a length of the third inner guidance slot is perpendicular to a length of each of the first and second inner guidance slots;
(e) a fourth inner guidance slot defined in the template assembly, wherein a length of the fourth inner guidance slot is perpendicular to the length of each of the first and second inner guidance slots;
(f) first, second, and third outer guidance slots defined in the frame assembly, wherein a length of the third outer guidance slot is perpendicular to a length of each of the first and second outer guidance slots;
(g) a fourth outer guidance slot defined in the template assembly, wherein a length of the fourth outer guidance slot is perpendicular to the length of each of the first and second outer guidance slots;
wherein the first, second, third, and fourth inner guidance slots define an area of tissue to be resected from a patient,
wherein the first, second, third, and fourth outer guidance slots define an area of tissue to be resected from a donor,
wherein the frame assembly is slidable in relation to the template assembly such that a size of the area of tissue to be resected from the patient and a size of the area of tissue to be resected from the donor are adjustable.

18. The template assembly of claim 17, wherein the first, second, and third outer guidance slots are disposed closer to an outer edge of the frame assembly than the first, second, and third inner guidance slots.

19. The template assembly of claim 17, wherein the size of the area of tissue to be resected from the donor is larger than the size of the area of tissue to be resected from the patient.

20. A template for resecting a tissue region, comprising:
(a) a template assembly having a surface for contacting a naturally occurring tissue region;
(b) a frame assembly comprising:
  (i) first and second inner guidance slots defined along the frame assembly, wherein the first and second inner guidance slots are spaced relative to one another to define a width of tissue to be resected from a patient;

(ii) a third inner guidance slot defined along the frame assembly, wherein a length of the third inner guidance slot is perpendicular to a length of each of the first and second inner guidance slots and wherein the third inner guidance slot defines a length of the tissue to be resected from the patient;

(iii) first and second outer guidance slots defined along the frame assembly and aligned adjacent to the first and second inner guidance slots, wherein the first and second outer guidance slots are positioned closer to an outer edge of the frame assembly in relation to the first and second inner guidance slots, wherein the first and second outer guidance slots are spaced relative to one another to define a width of tissue to be resected from a donor, wherein the width of tissue to be resected from the donor is greater than the width of tissue to be resected from the patient; and (iv) a third outer guidance slot defined along the frame assembly and aligned adjacent to the third inner guidance slot, wherein the third outer guidance slot is positioned closer to the outer edge of the frame assembly in relation to the third inner guidance slot, wherein a length of the third outer guidance slot is perpendicular to a length of each of the first and second outer guidance slots and wherein the third outer guidance slot defines a length of the tissue to be resected from the donor, wherein the frame assembly is translatable relative to the template assembly.

* * * * *